United States Patent
Hogue

(10) Patent No.: US 10,453,264 B1
(45) Date of Patent: Oct. 22, 2019

(54) SYSTEM FOR SIMULATING A VIRTUAL FITNESS PARTNER

(71) Applicant: 5 Stone Patents, Austin, TX (US)

(72) Inventor: Mark Wayne Hogue, Austin, TX (US)

(73) Assignee: Stone Patents, Austin, TX (US)

( * ) Notice: Subject to any disclaimer, the term of this patent is extended or adjusted under 35 U.S.C. 154(b) by 12 days.

(21) Appl. No.: 15/945,994

(22) Filed: Apr. 5, 2018

(51) Int. Cl.
- *G06T 19/00* (2011.01)
- *G06F 3/01* (2006.01)
- *G02B 27/01* (2006.01)
- *H04W 4/80* (2018.01)

(52) U.S. Cl.
CPC ........ *G06T 19/006* (2013.01); *G02B 27/0172* (2013.01); *G06F 3/012* (2013.01); *G02B 2027/0141* (2013.01); *G02B 2027/0178* (2013.01); *H04W 4/80* (2018.02)

(58) Field of Classification Search
CPC .................................................. H04N 5/7491
See application file for complete search history.

(56) References Cited

U.S. PATENT DOCUMENTS

| | | |
|---|---|---|
| 4,550,984 A | 11/1985 | Reymond |
| 6,091,546 A | 7/2000 | Spitzer |
| 8,817,092 B2 | 8/2014 | Wilkinson |
| 9,311,753 B2 | 4/2016 | Wilkinson |
| 2015/0379351 A1* | 12/2015 | Dibenedetto ...... G06K 9/00671 345/633 |
| 2017/0151481 A1 | 6/2017 | Divine |
| 2018/0268738 A1* | 9/2018 | Miller .................. G09B 19/003 |

FOREIGN PATENT DOCUMENTS

WO    WO2006134427 A1    12/2006

* cited by examiner

*Primary Examiner* — Priyank J Shah
(74) *Attorney, Agent, or Firm* — Garlick & Markison; Bruce E. Stuckman

(57) ABSTRACT

A method for execution by a mobile communications device includes generating display data, where a display device of eyewear, worn by a user performing a fitness activity, displays a virtual fitness partner in accordance with the display data to virtually superimpose the virtual fitness partner upon physical surroundings viewed by the user through at least one translucent lens of the eyewear to simulate performance of the fitness activity by the virtual fitness partner along a virtual transit within a physical vicinity of the user throughout the transit of the user. The virtual fitness partner is displayed in accordance with perspective data generated based on the user's transit velocity and head orientation, determined based on sensor data collected by at least one motion sensor. The virtual fitness partner is further depicted to perform one of a plurality of fitness partner actions in accordance with event trigger monitoring data.

20 Claims, 15 Drawing Sheets

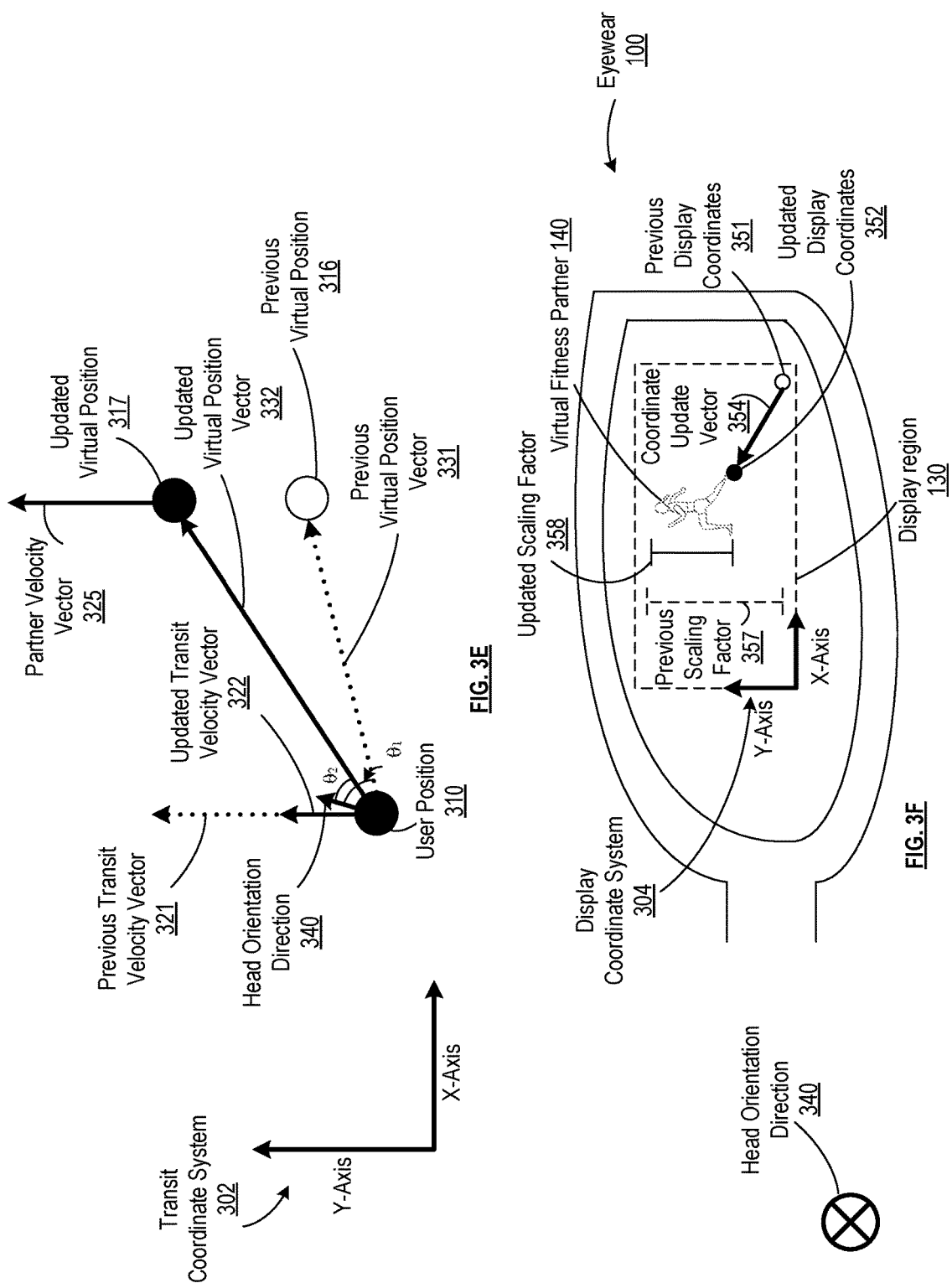

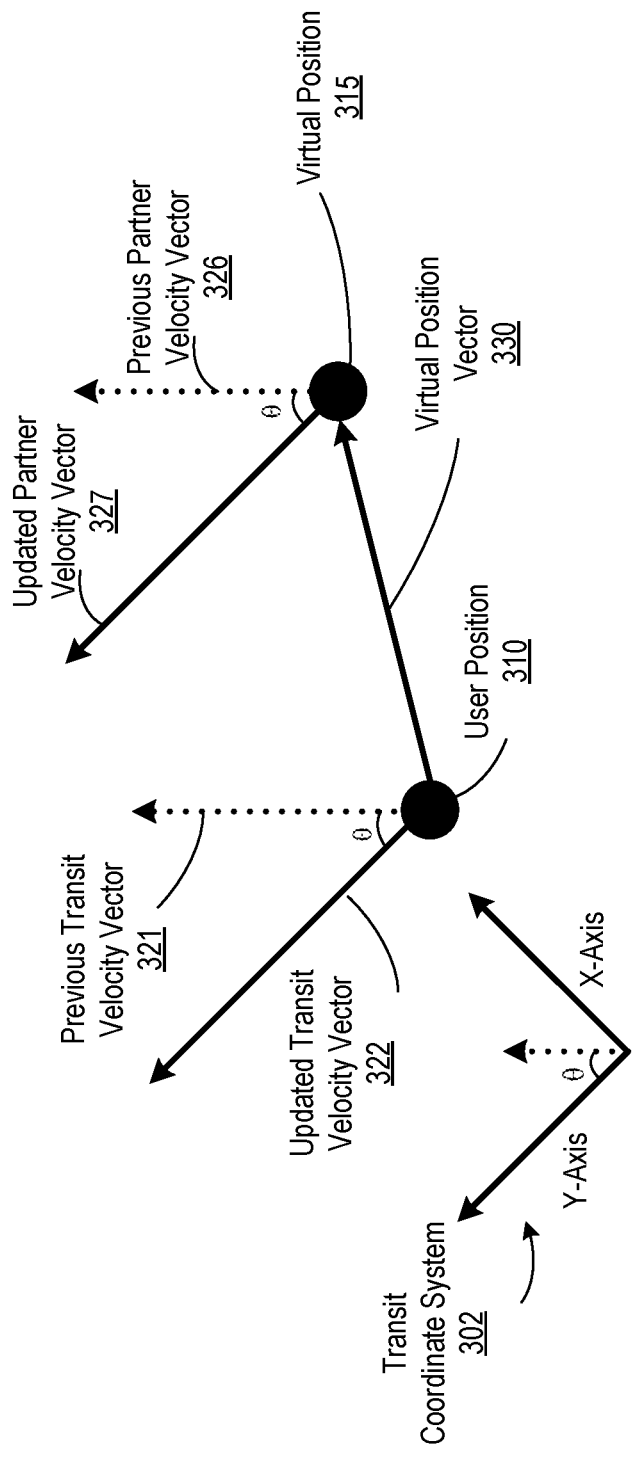

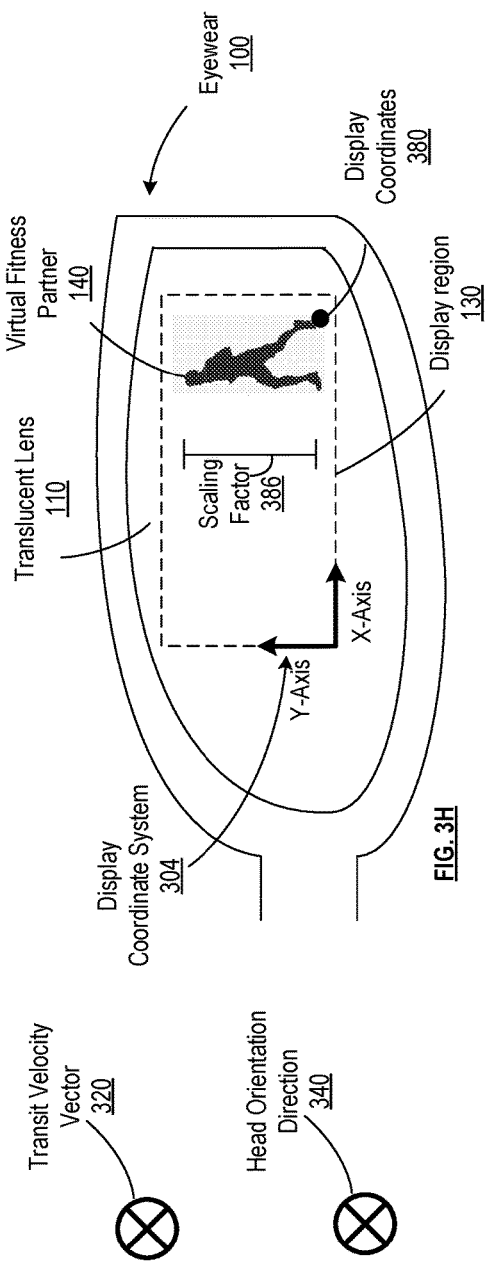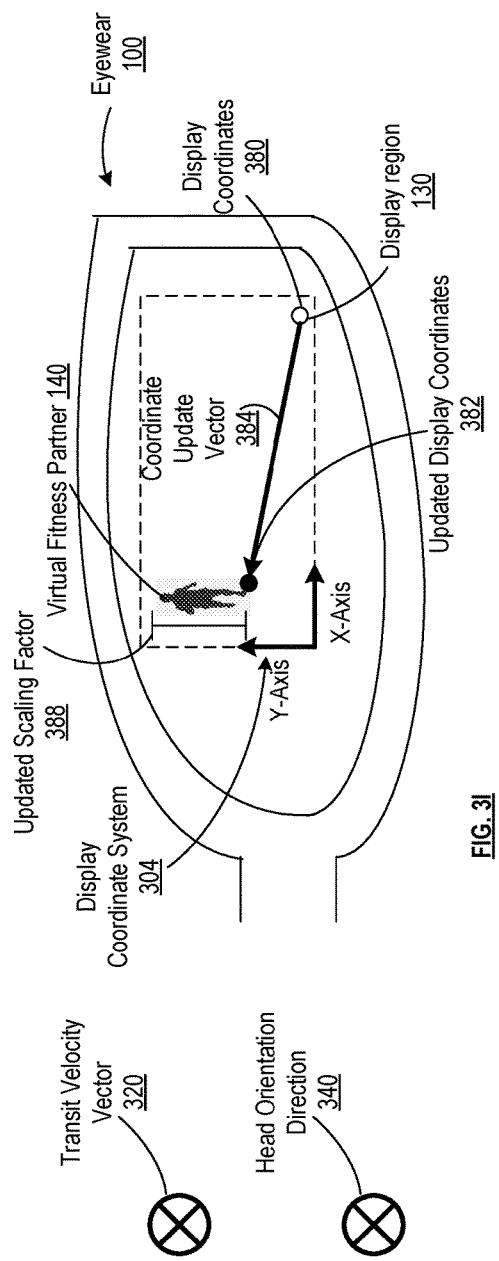
FIG. 3H
FIG. 3I

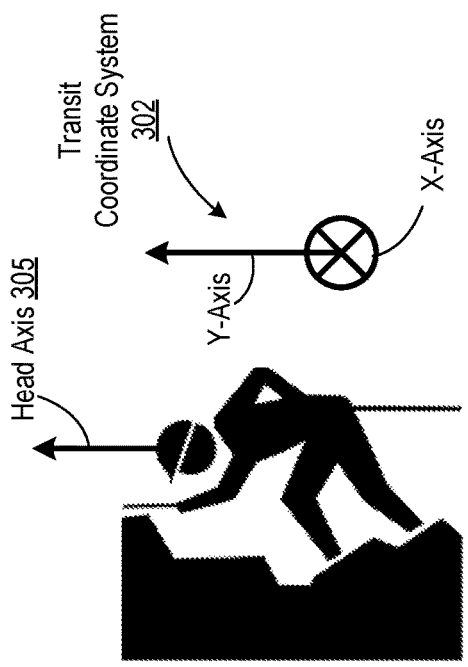
FIG. 3J
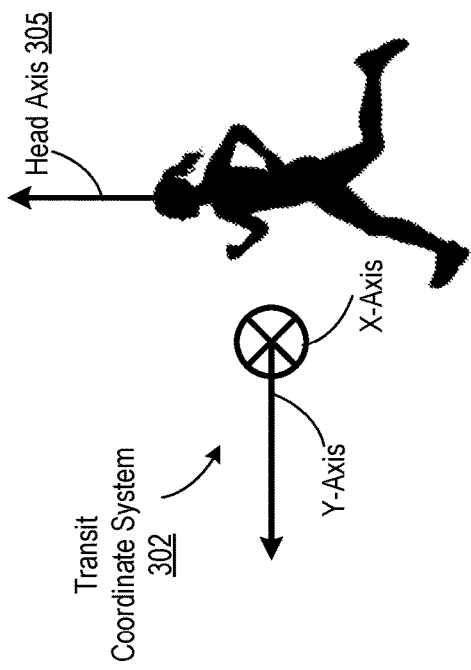
FIG. 3K
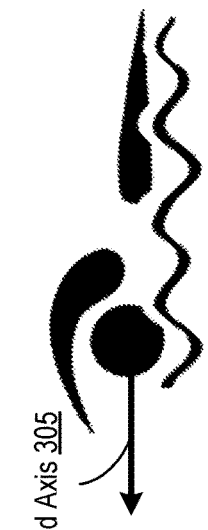
FIG. 3L
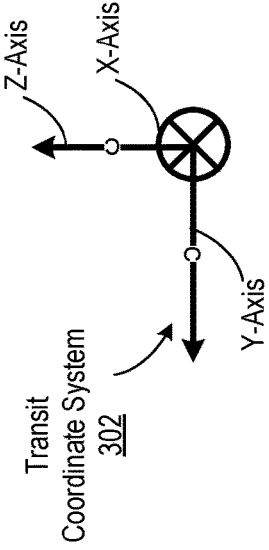

US 10,453,264 B1

SYSTEM FOR SIMULATING A VIRTUAL FITNESS PARTNER

CROSS-REFERENCE TO RELATED APPLICATIONS

None.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND OF THE INVENTION

Technical Field of the Invention

This invention relates generally to augmented, head-mounted displays, and communication systems.

Description of Related Art

BRIEF DESCRIPTION OF THE SEVERAL VIEWS OF THE DRAWING(S)

FIG. 3E is a diagram that illustrates the relationship between a user position, a transit velocity vector, a virtual position vector, a partner velocity vector, and a head orientation direction in accordance with various embodiments of the present invention;

FIG. 3F is a graphical illustration of a display device, demonstrating the relationship between the virtual position vector and the head orientation direction of FIG. 3E, and a scaling factor and display coordinates of a virtual fitness partner in accordance with various embodiments of the present invention;

FIG. 3G is a diagram that illustrates the relationship between a user position, a transit velocity vector, a virtual position vector, and a partner velocity vector in accordance with various embodiments of the present invention;

FIGS. 3H-3I are graphical illustrations of a display device, demonstrating how a virtual fitness partner can be displayed in multiple two dimensional views in accordance with various embodiments of the present invention;

FIGS. 3J-3L are graphical illustrations of users performing different types of fitness activities, demonstrating the relationship between a transit coordinate system and a head axis in accordance with various embodiments of the present invention;

DETAILED DESCRIPTION OF THE INVENTION

Figure 1:
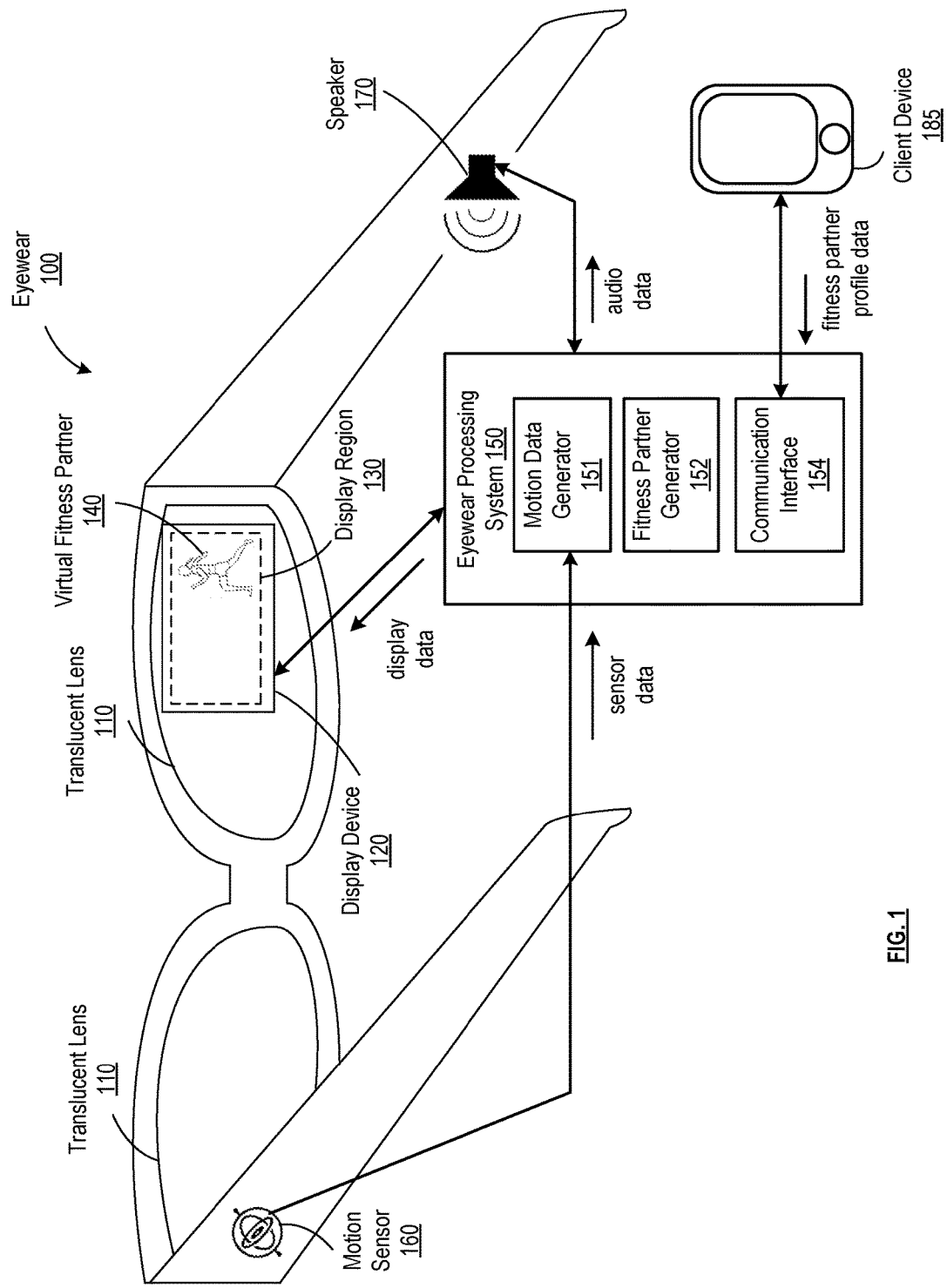
FIG. 1 is a schematic block diagram of eyewear in accordance with various embodiments of the present invention.

FIG. 1 presents a graphical illustration of an embodiment of the present invention that includes eyewear 100. The eyewear 100 can include one or more translucent lenses 110. All of, or a region of, one or more of the translucent lenses 110 can include a display region 130. At least one virtual fitness partner 140 can be displayed within the display region 130 via a display device 120, in accordance with display data received from an eyewear processing system 150. The eyewear 100 can be operable to virtually superimpose the virtual fitness partner 140 upon physical surroundings viewed by a user wearing the eyewear 100 through the at least one translucent lens 110 to simulate performance of a fitness activity by the virtual fitness partner 140 alongside, in front of, or otherwise within a physical vicinity of, the user.

The eyewear processing system 150 can include a motion data generator 151, a fitness partner generator 152, and/or a communication interface 154. The eyewear processing system can generate the display data based on motion data generated by the motion data generator 151 and further based on fitness partner profile data, for example, received from a client device 185 via short range communication and/or network communication to communication interface 154. The eyewear processing system 150 can be integrated within the eyewear 100 and/or can otherwise communicate with eyewear 100, for example, via a communication interface integrated within eyewear 100. The eyewear processing system 150 is discussed in further detail in the discussion of FIG. 2.

In some embodiments, the eyewear 100 can further include at least one motion sensor 160, for example, integrated within the eyewear and operable to collect sensor input corresponding head motions of the user and/or other motions made by the user. This sensor input can be utilized by the eyewear processing system 150 to generate some or all of the motion data.

In some embodiments, the eyewear 100 can further include at least one speaker 170, for example, corresponding to the location of one or both ears of the user when worn by the user. The one or more speakers 170 can generate sound, in accordance with audio data received from the eyewear processing system 150, to simulate the at least one virtual fitness partner 140 speaking to the user, or otherwise providing audio feedback to the user.

A fitness partner can provide the motivation and companionship needed to effectively complete a strenuous workout, exercise, or other fitness activity. In particular, during a fitness activity that involves a transit along a predetermined or dynamically determined route, it can be motivational to have a fitness partner performing the fitness activity alongside. Furthermore, receiving visual and/or vocal feedback, for example motivational feedback, critical feedback, and/or coaching from a fitness partner can further enhance performance of a fitness activity. A fitness partner can further alleviate navigational and/or route decision-making responsibilities during a workout, for example, by leading the way and/or providing navigational instructions. Finally, a fitness partner can monitor hazardous situations and provide visual and/or vocal warnings when a hazardous situation is detected.

An ideal fitness partner should always be available at desired workout times; should be able to maintain an ideal pace, while not far exceeding the ideal pace; and should be motivational in nature. However, an ideal fitness partner that can be difficult to find. The present invention introduces a solution to this problem by providing a user with a customizable, virtual fitness partner. A user can wear eyewear 100 during a fitness activity and can see their virtual fitness partner 140 performing the fitness activity alongside, ahead, behind, or otherwise within their physical vicinity. The user can perform the physical activity safely with, other than the virtual fitness partner superimposed upon their physical surroundings in their peripheral vision and/or another portion of their field of view, an otherwise normal field of view of their physical surroundings through the one or more translucent lenses 110. The virtual fitness partner can be depicted to perform the same fitness activity as the user for some or all of the duration of a user's workout.

As used herein, the fitness activity can include running, jogging, walking, hiking, climbing, road biking, mountain biking, motocross, snowmobiling, swimming, surfing, skiing, snowboarding, roller skating, roller blading, ice skating, or another physical activity associated with a transit of the user. In some embodiments, the transit can include a simulated transit utilizing stationary exercise equipment such as a treadmill, elliptical machine, stair-stepping machine, stationary bicycle. In some embodiments, the fitness activity can include non-transit activities such as yoga, Pilates, high intensity interval training (HIIT), strength conditioning, weight lifting, or other physical activities that may not include a transit, but would still benefit from a virtual fitness partner, for example, acting as a virtual fitness coach or otherwise leading the fitness activity within the vicinity of the user.

At one or more times during the duration of the workout, the virtual fitness partner 140 can also be depicted to perform one or more of a plurality of fitness partner actions, such as encouraging visual and/or auditory feedback and/or a change in virtual pace and/or direction. These fitness partner actions can be triggered by the detection of one or more of a plurality of corresponding event trigger conditions by the eyewear processing system 150. The display data and/or the audio data generated by the eyewear processing system 150 can reflect the identified one or more fitness partner actions in response to detection of the corresponding one or more event trigger conditions.

For example, the virtual fitness partner can be configured to run at a configured, set pace. The user can prompt their virtual fitness partner, via a voice command such as "increase pace" or other user input, to increase or decrease their virtual pace by a preset, incremental measure, from the preset pace. The virtual fitness partner will be depicted to perform the fitness activity at this increased and/or decreased virtual pace in response. The preset incremental measure can be the same or different for increase and decrease in pace, and can be configured by the user. Throughout the activity, the user can continue to increase and/or decrease the pace of their virtual fitness partner via the voice commands or other user input by the preset incremental measure. The user can also prompt their virtual fitness partner to return to the configured preset pace via a voice command such as "reset pace" or other user input. In some embodiments, the eyewear itself or other elements of the eyewear processing system can include buttons or other physical means of user input for this purpose, and some or all of the user input can include input induced by the user pressing or otherwise interacting with the buttons. For example, the system can include "+" and "−" buttons corresponding to increasing and decreasing pace by the preset incremental measure, respectively.

The eyewear 100 can include custom and/or modified glasses, sunglasses, swimming goggles, protective goggles, eyewear corresponding to fitness activity equipment, contact lenses, or other eyewear that utilizes Augmented Reality (AR) and/or a heads-up display technology to superimpose the virtual fitness partner upon the physical surroundings. In some embodiments, the eyewear 100 can include an optical head-mounted display, and/or the one or more translucent lenses 110 can include partly silvered mirrors and/or semi-transparent mirrors that allow the user to see the true physical surroundings though at least one translucent lens 110, and that also enable the display data to be projected onto and/or reflected off of the real imagery to pass through the at least one translucent lens 110. The display device 120 can be operable to project the virtual fitness partner 140 upon the partly silvered mirrors and/or the semi-transparent mirrors to be reflected for display to the user. In some embodiments, the eyewear 100 can include a head-mounted display, and/or the display device 120 device can include one or more cathode ray tubes, liquid crystal displays, liquid crystal on silicon, organic light-emitting diodes, and/or display screen that is embedded within the translucent lens 110, in front of the translucent lens 110, or behind the translucent lens 110, in a location corresponding to the display region 130. The display device 120 and/or at least one translucent lens 110 can also be operable to display the virtual fitness partner via any other display technology. The display device 120 can be operable to display the virtual fitness partner 140 upon the display screen in accordance with the display data. In some embodiments, one or more cameras of the eyewear processing system 150 can capture physical surrounding image data that includes a portion of the field of view of the user corresponding to display region 130, and the display data generated by the eyewear processing system 150 can include the virtual fitness partner superimposed upon the physical surrounding image data for display by a display screen in display region 130.

In some embodiments, the eyewear 100 includes two translucent lenses 110, corresponding to each of the user's eyes. The display region 130 can include separate regions upon each of the two translucent lenses 110 corresponding to each of the user's eyes, and a single display device 120, or two separate display devices 120 corresponding to the two translucent lenses 110, can display the virtual fitness partner in accordance with stereoscopic display data received from the eyewear processing system 150. For example, the stereoscopic display data can indicate left eye display data and right eye display data. The portion of the display region 130 corresponding to the translucent lens 110 associated with the left eye can display the left eye display data of the stereoscopic display data, and the portion of the display region 130 corresponding to the translucent lens 110 associated with the right eye can display the right eye display data of the stereoscopic display data.

In other embodiments, the display data is monoscopic display data. In such embodiments, the virtual fitness partner can be displayed upon only one of the two lenses, for example, corresponding to a user's peripheral vision. In other embodiments, the display region is viewed by both eyes and displays the virtual fitness partner as a monoscopic display.

In various embodiments of the present invention, eyewear 100, configured to be worn by a user while performing a fitness activity, includes at least one sensor such as motion sensor 160 or another sensor configured to register motions made by the user, and/or at least one translucent lens 110, where a surface of the at least one translucent lens includes a display region 130.

The eyewear 100 can also include, or otherwise communicate with, a motion data generator 151 that includes at least one processor and memory. The motion data generator 151 processes sensor data collected by the at least one sensor, such as motion sensor 160, other sensors of the eyewear processing system, and/or sensors of the client device 185, to generate motion data. The motion data can include a transit velocity vector corresponding to a transit of the user during the fitness activity that indicates a transit pace and a transit direction, and/or can include head tracking data corresponding to head movement of the user that indicates a head orientation direction relative to the transit direction.

The eyewear 100 can also include, or otherwise communicate with, a communication interface 154 that receives fitness partner profile data. The fitness partner profile data can be configured by the user by utilizing a client application associated with the eyewear via input to an interactive interface displayed by a client device associated with the user, such as client device 185.

The eyewear 100 can also include a fitness partner generator that generates display data associated with a virtual fitness partner. The display data can be generated based on appearance data corresponding to an appearance of the virtual fitness partner. The appearance data can be determined based on the fitness partner profile data. Alternatively or in addition, the display data can be generated based on perspective data that indicates a display size and display coordinates calculated based on a virtual position vector and the head orientation direction. The virtual position vector can be determined based on calculating relative velocity data based on the transit velocity vector and a partner velocity vector, and the virtual position vector can indicate a magnitude and a direction of a virtual position of the virtual fitness partner relative to a position of the user. Alternatively or in addition, the display data can be generated based on event trigger monitoring data, determined based on the motion data. The event trigger monitoring data can indicate one of a plurality of fitness partner actions in response to the fitness partner generator determining that a corresponding one of a plurality of event trigger conditions has been met.

The eyewear 100 can include a display device that displays the virtual fitness partner within the display region in accordance with the display data to virtually superimpose the virtual fitness partner upon physical surroundings viewed by the user through the at least one translucent lens to simulate performance of the fitness activity by the virtual fitness partner along a virtual transit within a physical vicinity of the user throughout the transit of the user, where the virtual fitness partner is depicted to perform the one of the plurality of fitness partner actions in accordance with the event trigger monitoring data.

Figure 2:
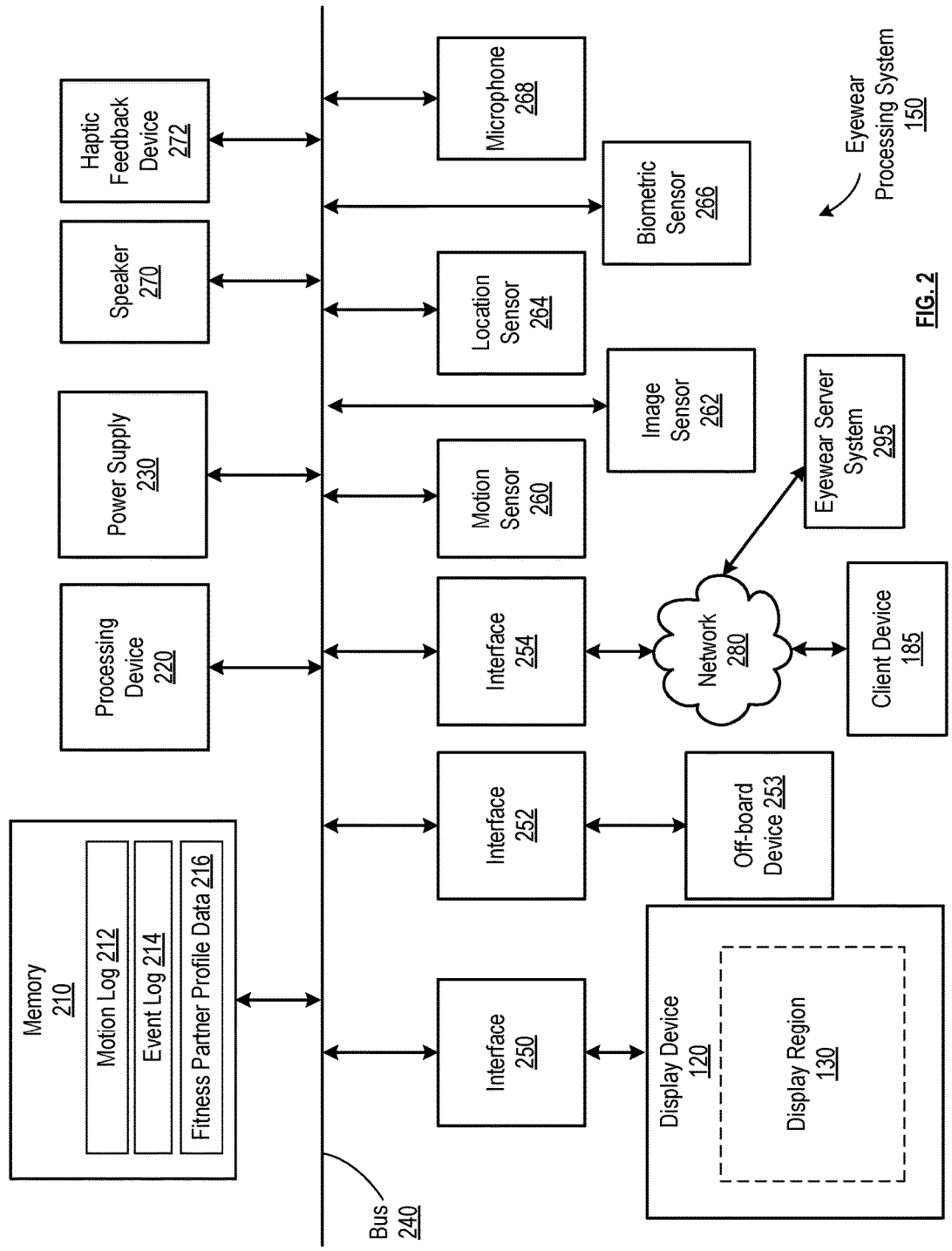
FIG. 2 is a schematic block diagram of an eyewear processing system in accordance with various embodiments of the present invention.

FIG. 2 presents an embodiment of the eyewear processing system 150. The eyewear processing system can include at least one memory 210, at least one processing device 220, and/or at least one interface 250 that communicates with display device 120, all communicating via bus 240. For example, at least one memory 210 can store operational instructions, that, when executed by the at least one processing device 220, causes the at least one processing device 220 to generate the display data to be sent to the display device 120 via the interface 250. The at least one memory 210 can also store motion log 212, event log 214, fitness partner profile data 216, other user profile data, and/or application data associated with the eyewear processing system 150. The eyewear processing system 150 can include at least one power supply 230, such as a disposable or rechargeable battery, to power elements of the eyewear processing system 150.

The eyewear processing system 150 can also include one or more communication interfaces, such as interface 250 operable to send display data to display device 120 for display on display region 130 via wired and/or wireless communication; interface 252 operable to communicate with an off-board device 253, worn or carried by the user, via short range wired and/or wireless communication; and/or interface 254 operable to communicate with a client device 185 and/or an eyewear server system 295 via a wired and/or wireless communications network 280. Interface 252 and/or interface 254 can be utilized to implement communication interface 154 of FIG. 1. Interfaces 250, 252, and/or 254 can be implemented by utilizing a short range wireless communication transceiver, wireless local area network transceiver, cellular data transceiver, a wired communication connection, and/or other communications interface.

Some or all of the elements of the eyewear processing system 150 of FIG. 2 and discussed herein can be integrated within the eyewear 100 itself in an on-board portion of the eyewear processing system 150. For example, a circuit board that includes at least one memory 210, at least one processing device 220, and/or at least one interface 250, 252 and/or 254 can be integrated within a temple, arm, bridge, and/or strap of the eyewear, and/or can otherwise be physically attached to the eyewear 100.

Alternatively, some or all components of the eyewear processing system 150 of FIG. 2 and discussed herein can be integrated within one or more off-board devices 253, and can thus communicate with the on-board portion of the eyewear processing system 150 via interface 252. For example, interface 252 can be integrated within the on-board component and receive data from some or all additional components of the eyewear processing system 150 integrated within the one or more off-board devices 253. One or more off-board devices 253 can also be worn, carried by, attached to, or otherwise coupled to the user, and/or fitness equipment used by the user, during the fitness activity, and can include a smartphone associated with the user; a smartwatch, fitness tracker, and/or other wearable technology worn by the user; a client device associated with the user such as client device 185; and/or a custom off-board component. The off-board device 253 can communicate with interface 252 via short range wireless communication such as Bluetooth, ZigBee, near field communication, ultra-wide band communication, and/or another short range wireless communication protocol. For example, the off-board device 253 can be paired to the eyewear processing system via the short range wireless communication protocol while the user is engaging in the fitness activity. Alternately or in addition, the off-board device 253 can communicate with interface 252 via a wired connection. In some embodiments, at least one off-board device 253 can include at least one power supply 230, for example, including a back-up power reserve of the eyewear processing system 150.

Some or all additional components of the eyewear processing system 150 of FIG. 2 and discussed herein can communicate with on-board or off-board components via Wi-Fi, cellular, and/or other wireless communications via a wired and/or wireless network 280 by utilizing interface 254. For example, the eyewear processing system can receive data from a client device such as client device 185, a server associated with the eyewear processing system such as eyewear server system 295, and/or the Internet. For example, the eyewear processing system can receive user profile data, which can include some or all of the fitness partner profile data 216, map and/or navigation data, application data generated by the client device, configuration data, or other data used by the eyewear processing system. Alternatively or in addition, the interface 254 can transmit some or all data generated by the eyewear processing system 150 to a client device 185 and/or eyewear server system 295.

The eyewear processing system can include at least one speaker 270. The at least one speaker 270 can include speaker 170 of FIG. 1, integrated within the eyewear 100 itself. The at least one speaker 270 can include wired and/or wireless headphones and/or earbuds, for example, receiving audio data from the on-board component, the client device 185, and/or an off-board device 253 via a wired auxiliary cable connection or wireless short range communication connection. In various embodiments, the off-board device can include headphones, earbuds, or other speakers that can be heard by the user communicating directly with the eyewear processing system 150 via the wired and/or wireless short range communication with interface 252.

The eyewear processing system can include at least one haptic feedback device 272 that can be configured to deliver vibrations, pressure, or other haptic feedback to the user, for example, in conjunction with the one or more of the plurality of fitness partner actions. The haptic feedback device can be included in the off-board device 253, for example, worn in other locations of the user's body. For example, an off-board device 253 integrated within gloves worn by the user that includes a haptic feedback device 272 can deliver haptic feedback to the user in conjunction with the eyewear processing system determining that the virtual fitness partner perform a fitness partner actions that includes giving a high-five, where the haptic feedback delivered to the user simulates receiving a high-five from the virtual fitness partner. Other motivational physical contact by the virtual fitness partner, such as a chest bump or a pat on the shoulder, can be simulated by other haptic feedback devices located on corresponding portions of the body of the user.

The eyewear processing system 150 can include one or more sensor devices, such as at least one motion sensor 260 operable to collect motion data, at least one image sensor 262 operable to collect image data, at least one location sensor 264 operable to collect location data, at least one biometric sensor 266 operable to collect biometric data, and/or at least one microphone 268 operable to collect audio data. Some or all of the sensors can be integrated within one or more off-board devices 253 and/or client devices 185, and the sensor data and/or additional input data can be collected from the one or more off-board devices 253 and/or client devices 185 via interface 252 and/or 254, respectively.

The at least one motion sensor 260 can be operable to collect motion data corresponding to motions made by the user. The at least one motion sensor 260 can include, for example, one or more gyroscopes, one or more accelerometers, one or more pedometers, one or more altimeters, one or more cameras, and/or other sensors that can detect motions performed by the user. In some embodiments, for example, where the fitness activity includes biking, cycling, motocross, skateboarding, and/or a fitness activity where transit velocity is associated with Revolutions Per Minute (RPM), the motion sensors 260 can include speed sensors and/or cadence sensors, for example, attached to a bicycle ridden by the user during the fitness activity. The at least one motion sensor 260 can include the motion sensor 160 of FIG. 1, integrated within the eyewear 100.

In some embodiments, the at least one motion sensor 260 can be utilized by the eyewear processing system to generate transit velocity data corresponding to a transit of the user during the fitness activity, which can indicate a transit pace such as a speed, a step rate, and/or RPM; and and/or transit direction such as a cardinal direction and or relative direction determined by measuring change in direction. The at least one motion sensor 260 can also be utilized by the eyewear processing system to generate head tracking data corresponding to head movement of the user, which can indicate a head orientation direction relative to the transit direction and/or a head turning rate indicating the rate of change in the head orientation. In some embodiments, the at least one motion sensor 260 can also be utilized to detect gestures by the user corresponding to gesture command input to the eyewear processing system 150.

The at least one image sensor 262 can include, for example, one or more cameras and/or other image sensors operable to collect image data corresponding to the user's surroundings. The image data can be utilized by the eyewear processing system 150 perform object recognition and/or object tracking by utilizing a computer vision processing system or other image processing techniques. For example, the object tracking data can be used to determine changes in position of a detected object relative to the user, which can be used to determine some or all of the transit velocity data and/or head orientation data. Alternatively or in addition, the image data can be utilized the eyewear processing system 150 to determine the virtual position of the virtual fitness partner and/or the perspective data such that the virtual fitness partner is superimposed upon the physical surroundings relative to at least one detected and/or tracked object. The object recognition and/or object tracking can also trigger one or more of the plurality of fitness partner actions.

In some embodiments the object recognition and/or object tracking can be utilized by the eyewear processing system 150 to detect a path corresponding to the transit of the user. As used herein, a path can include a footpath, road, trail, track, bike lane, sidewalk, swimming lane, other designated surface on which the user performs the fitness activity, and/or other designated three-dimension region or route within which the user performs the fitness activity. For example, the user can follow the direction of the path during their transit, and remain within a width, orthogonal to the direction of transit, and designated by boundaries of the path. Detection of the path can be used to virtually depict the virtual fitness partner moving along the path, for example, within the boundaries of the path and/or in a predetermined area along the route. Detection of the path can also be used to determine a current location of the user and/or the direction of travel of the virtual fitness partner, for example, if the path corresponds to a known route for the transit with corresponding location and/or navigation data.

In some embodiments, the object recognition and/or object tracking can be utilized by the eyewear processing system 150 to detect physical barriers, people, and/or other physical impedances or obstructions that are along the virtual route corresponding to the virtual transit of the virtual fitness partner. Detection of these physical objects can be utilized by the eyewear processing system to visually depict the virtual fitness partner avoiding such barriers. For example, the virtual fitness partner can be depicted to move around people along the path, dodge barriers, hurdle over a tree stump, duck under low hanging trees the barrier, or otherwise avoiding the detected barriers. In some embodiments, the virtual fitness partner can be depicted to interact physically with such barriers, and can, for example, be depicted to collide into a tree, trip on a curb and fall, splash in a puddle, slip on an icy portion of the path, swing on a low hanging tree branch, swing around a light pole, stumble on boulders, run up stair steps, jump to slap a street sign, wave at and/or high-five an actual runner moving in the opposite direction, pat the head of a dog along the path, and/or otherwise be depicted to interact with physical objects.

In some embodiments, the detected barriers can correspond to potential hazards for the user. For example, the virtual fitness partner can be depicted to warn the user of physical hazards along the projected route of the user and detected by the eyewear processing system. For example, puddles, ice, sharp objects, untied shoelaces of the user, curbs, slippery surfaces, approaching vehicles, and/or other hazards can be detected and the user can be alerted by the eyewear processing system. For example, the eyewear processing system can generate additional image data that is superimposed upon and/or within the vicinity of the hazards, such as highlighting the hazard, circling the hazard, and/or pointing at the hazard, for display to the user by the display device 120. In some embodiments, the virtual fitness partner can be depicted to visually and/or audibly alert the user, for example, depicted to point and the hazard and/or interact with the hazard by colliding with the hazard, tripping on the hazard, avoiding the hazard, and/or can be depicted to vocally alert the user by saying "look out for the curb" or "your shoelaces are untied" for delivery to the user via the at least one speaker 270.

In some embodiments, the image sensor can detect traffic signals, traffic signs, and/or passing cars at an intersection. This can be used to determine when a user is at a street intersection or otherwise needs to abide by traffic laws. The traffic laws can also be determined based on the user activity, for example, whether the user is determined to be jogging or biking and thus needs to follow pedestrian traffic laws or biking traffic laws, accordingly. The traffic laws and the detected traffic signals can be used to determine that a traffic law must be followed in conjunction with one or more event trigger conditions. For example, the virtual fitness partner can be depicted to stop at a stop sign, to yield to an oncoming car at a roundabout, to stop moving at a red traffic light and begin moving in response to determining the traffic light has turned green, wait at a crosswalk until the crosswalk signal indicates pedestrians are allowed to cross, wait at a crosswalk until there is no detected oncoming traffic, and/or can visually and/or vocally alert the user of the traffic law to be abided.

Alternatively or in addition, one or more image sensors 262 can be operable to collect image data corresponding to eye tracking of the user's eyes, which can be utilized by the eyewear processing system 150, for example, to supplement the head orientation direction in determining a direction of the user's gaze. This can be utilized to determine when the user is looking at the virtual fitness partner, even if the user's head is not oriented toward the virtual fitness partner and thus the virtual fitness partner is not centered within the user's field of view, for example, to trigger one or more of the plurality of fitness partner actions.

The location sensor 264 is operable to collect location data corresponding to, or used to determine, the current position of the user. For example, the location sensor can include a Global Positioning System (GPS), compass, and/or a barometer. The location sensor can include at least one transceiver and can be operable to triangulate the location based on receiving signals from nearby cell towers and/or Wi-Fi hotspots. The location data can be collected via off-board devices 253, such as a smart device paired to the eyewear processing system 150, and the location data can correspond to location data of the smart device. The location data can be further generated based on map data stored in memory 210, received as application data, and/or downloaded from the Internet. The location data can be further generated based on the object recognition performed based on the image data, for example, where the recognized object corresponds to a known location determined based on past location data and/or past transits by the user along the same route, stored in memory 210, received as application data, and/or downloaded from the Internet. For example, the recognized objects can include street signs, natural features, distinct buildings, landmarks, the user's home, and/or other distinct objects with a known location. The location data can further be generated based on object tracking data generated based on the image data and/or the motion data, for example, to determine and track relative position with respect to the recognized object.

The location data can be used to track the route of the fitness activity to generate route data, such as a route log stored in memory 210 that includes a plurality of time-stamped locations. The location data can be used to determine navigation data with respect to a predetermined route and/or predetermined destination corresponding to the fitness activity. The navigation data can be used to determine the partner velocity vector of the virtual fitness partner, for example, to simulate the virtual fitness partner following the predetermined route and/or navigating towards the predetermined destination. The navigation data and/or other location data can be used to trigger one or more of the plurality of fitness partner actions.

The at least one biometric sensor 266 is operable to collect biometric data corresponding to the user. For example, the at least one biometric sensor 266 can monitor heart rate and/or blood pressure. This can be used to determine health data for the user, such as calorie burning data corresponding to the fitness activity. This can also be used to determine hazardous health conditions, such as dangerous heart rate or blood pressure. The biometric data and/or determination that the user is undergoing a hazardous health condition, can be utilized to trigger one or more of the plurality of fitness partner actions such as a visual or vocal alert to the user that they are undergoing a dangerous health condition and/or that the user should cease performance of the activity. In some embodiments the eyewear processing system can automatically alert emergency services and/or a configured emergency contact, and can send biometric data and/or location data to the emergency services and/or configured emergency contact.

The at least one microphone 268 is operable to collect audio data, such as voice command data corresponding to the user. For example, the voice command data can be used to trigger one or more of the of the plurality of fitness partner actions, and/or can be used to configure navigation data, fitness partner profile data 216, application data, user profile data, and/or other settings of the eyewear processing system 150. The at least one microphone can also be operable to collect breathing data, for example, to determine a breathing rate and/or heaviness of breath of the user. This can be used in conjunction with the biometric data to determine the health data and/or the hazardous health condition data corresponding to the user. Audio data collected by the at least one microphone 268 can also be used in conjunction with the image data to generate object recognition data, based on detecting and recognizing a sound made by a detected object to aid in identifying the object. The at least one microphone 268 can also be used in conjunction with the image data to generate the object tracking data, based on determining a change in pitch and/or amplitude of a sound made by a detected object, for example, to aid in determining a relative position of the detected object with respect to the user.

The eyewear processing system 150 can generate motion data. For example, at least one memory 210 can store operational instructions, that, when executed by the at least one processing device 220, causes the at least one motion data generator to generate the transit velocity vector, the head orientation direction, and/or other head tracking data. Some or all of the raw and/or processed motion data can be stored in motion log 212, for example, as timestamped motion data entries and/or location tagged motion data entries based on location data captured at the time of the corresponding motion data of the motion data entry. In some embodiments, the motion data is generated by utilizing the at least one processing device 220 and at least one memory 210 to implement the motion data generator 151 of FIG. 1.

Alternatively or in addition, the eyewear processing system 150 can generate display data associated with a virtual fitness partner. For example, at least one memory 210 can store operational instructions, that, when executed by the at least one processing device 220, causes the at least one processing device 220 to generate the display data based on the motion data; additional sensor input collected by at least one sensor 260, 262, 264, 266, and/or 268; fitness partner profile data 216; and/or application data such as profile data and/or other application data stored in memory 210, collected from the client device 185, and/or collected from the eyewear server system 295. In some embodiments, the display data is generated by utilizing the at least one processing device 220 and at least one memory 210 to implement the fitness partner generator 152 of FIG. 1.

The display data generated by the eyewear processing system 150 can be sent to the display device 120, and the display device 120 can display the virtual fitness partner in accordance with appearance data and perspective data indicated in the display data. Alternatively, the display device can be sent the appearance data and/or the perspective data, and the display device can utilize the appearance data and/or perspective data to determine the display data based on parameters of the display device and/or based on parameters of the at least one translucent lens. In some embodiments, the display data can include stereoscopic display data, and can indicate left eye display data and right eye display data.

To generate the perspective data, the eyewear processing system can utilize motion data and/or other input data to determine a virtual position vector that indicates a magnitude and a direction of a virtual position of the virtual fitness partner relative to the user. For example, the virtual position vector can be determined based on calculating relative velocity data based on the transit velocity vector and a partner velocity vector associated with the virtual fitness partner. The partner velocity vector can be predetermined based on the fitness partner profile data 216, and/or can be calculated, for example, in real-time, based on the motion data, for example, where the pace and/or direction of the virtual fitness partner is set by the user pace. The partner velocity vector can be set and/or changed in response to one or more of the plurality of event trigger conditions. The relationship between the user position, the transit velocity vector, the virtual position vector, and the partner velocity vector is discussed in greater detail in the discussion of FIGS. 3A, 3C, and 3F.

The virtual position vector, along with the head orientation data, can be used to determine a display size, such as a scaling factor, of the virtual fitness partner, and can further indicate display coordinates of the virtual fitness partner. The relationship between the virtual position vector, the head orientation direction, and the scaling factor and display coordinates of the perspective data is discussed in greater detail in the discussion of FIGS. 3A-3G. The display size, scaling factor, and/or other perspective data can further be determined based on a determined field of view of the user and/or known parameters corresponding to the display device 120, the display region 130, the at least one translucent lens 110, and/or the eyewear 100.

The appearance data of the display data can correspond to an appearance of the virtual fitness partner. For example, the appearance data can be determined based on the fitness partner profile data 216 and/or other user profile data. The appearance data can be configured by the user via user input to the client device. The appearance data can be based on image data corresponding to a real person, such as a famous athlete, friend or other personal connection associated with the user, or the user themselves. The appearance data can include actual image data, for example, captured by camera, by image sensor 262 and/or retrieved via the network 280. The appearance data can also include computer generated image data, generated by the eyewear processing system 150, client device 185, eyewear server system 295, and/or generated externally and downloaded via the network 280. The appearance data can otherwise include avatar data used to generate the display depicting the virtual fitness partner.

The appearance data can be based on 180-degree, 270-degree or 360-degree view data corresponding to the virtual fitness partner, for example, included in the fitness partner profile data. For example, the view of the virtual fitness partner 140 will be different when viewed from the side, from the front, or from behind. Thus, the appearance data can be further generated by utilizing the perspective data and the 360-degree view data of the virtual fitness partner to determine a two-dimensional appearance of the virtual fitness partner in accordance with virtual position vector, the head orientation direction, and/or an orientation of the virtual fitness partner, for example, in accordance with the partner velocity vector.

The display data can further be generated based on event trigger monitoring data, generated by the eyewear processing system 150 based on the motion data and/or based on input data collected by the at least one sensor 260, 262, 264, 266, and/or 268. The event trigger monitoring data can indicate one or more of the plurality of fitness partner actions in response to the fitness partner generator determining that the corresponding one or more of the plurality of event trigger conditions has been met. The display data, audio data, and/or haptic feedback data can be generated to depict the one or more of the plurality of fitness partner actions. The visual depiction of one or more of the plurality of identified fitness partner actions can also be indicated in the appearance data. Any of the fitness partner actions described herein can correspond to any of the event trigger conditions described herein, and thus can be displayed and/or otherwise depicted in conjunction with display of the virtual fitness partner in response to any of the detected conditions as described herein.

The plurality of event trigger conditions can include determining that the user is looking at the virtual fitness partner, for example, by determining that the user has turned their head towards a virtual position of the virtual fitness partner and/or by determining the user's gaze is fixed on the display of the virtual fitness partner. In response to determining that the user is looking at the virtual fitness partner, in response to determining that the user has turned their head and/or gaze towards the virtual fitness partner, and/or in response to determining that the user changed from a state of looking away from the virtual fitness partner to looking towards the virtual fitness partner, the virtual fitness partner can perform a fitness partner action, such as giving an encouraging thumbs up.

The plurality of event trigger conditions can also be based on the transit pace of the user. For example, the eyewear processing system 150 can determine that the user is moving faster than a threshold and/or slower than respective, configured thresholds. In some embodiments, the plurality of event trigger conditions can be based on the magnitude of the gap between the user position and the position of the virtual fitness partner, and/or based on change in pace and/or direction of the user and/or the virtual fitness partner. For example, the eyewear processing system 150 can determine that the user is lagging farther behind the virtual fitness partner more than a configured threshold and/or has passed the virtual fitness partner beyond a configured threshold.

Detection of such trigger conditions can induce a corresponding fitness partner action. This can include motivational visual and/or auditory feedback, such as giving a thumbs up and/or saying one or more of "'sup?" "You can do it," "come on, keep up," "keep moving," "you're doing great," and/or "let's finish strong." The plurality of fitness partner actions can include critical visual and/or auditory feedback such as passing the user, shaking their head, laughter, and/or derogatory phrases such as "outta the way," "slowpoke," and/or "move it!"

The fitness partner actions can also include a change of pace and/or direction of the virtual fitness partner. Changes in virtual fitness partner velocity can be induced, for example, based on detecting a change of pace and/or direction of the transit velocity of the user, based on navigation data corresponding to a desired route, based on the physical surroundings detected by the eyewear processing system 150, and/or can based on other input data to the eyewear processing system 150.

The plurality of fitness partner actions can include coaching actions, which can include auditory feedback that includes coaching instruction such as "raise your knees more," "try increasing your stride," "try to take longer, deeper breaths," "kick harder," and or other coaching instruction. The coaching actions can also include corresponding visual feedback, where the virtual fitness partner is depicted to perform the corresponding action, for example, depicted to raise their knees high, depicted to increase their stride, depicted to take longer, deeper breaths, and/or depicted to kick harder, respectively. The virtual fitness partner can be depicted to say "watch me!" before performing the corresponding action. The corresponding event trigger condition can correspond to the eyewear processing system 150 determining that performance of the corresponding activity by the user compares unfavorably to proper technique, based on corresponding motion data, speaker data, biometric data, and/or other data generated by the eyewear processing system.

The appearance data can dictate the display of the performance of the activity differently for different fitness activities. For example, if the user is running, their virtual fitness partner can be depicted to be running as well, while if the user is biking, their virtual fitness partner can be depicted to be biking as well. The activity being performed by the user can be determined by the eyewear processing system 150 based on user input and/or user profile data, and/or can be determined in real-time during the activity based on the motion data and/or image data, where the eyewear processing system 150 automatically detects the activity being performed, and/or voice command and/or gesture command data can be used to allow the user to instruct the eyewear processing system 150 of the activity. The virtual fitness partner can be configured to perform a different activity from the user in some embodiments.

Furthermore, the form, style, or other characterizations of the physical motions depicted to perform the fitness activity by the virtual fitness partner can be included in the appearance data. In some embodiments, the form, style, or other characterizations of the physical motions made by the user during the activity can be detected to dictate the virtual fitness partner's form in performing the fitness activity. For example, the appearance data can indicate a form of performance of the fitness activity that automatically matches the detected form of the user's performance of the fitness activity. This can be included in one or more of the event triggering conditions and corresponding fitness partner action. For example, if a jogging user begins performing high-knees, the eyewear processing system 150 can detect the change to performing high-knees by the user and depict the performance of high-knees by the virtual fitness partner. As another example, a swimming user doing laps in a swimming pool may change from freestyle, breaststroke, backstroke, and/or butterfly stroke during their workout, and their virtual fitness partner can be depicted to change their strokes respectively in response to the eyewear processing system 150 detecting the current stroke performed by the user. In some embodiments, changes in stroke and/or other activity type can be preset in the fitness partner profile data, dictating time intervals and/or laps corresponding to performance of each stroke and/or other activity type by the virtual fitness partner. In some embodiments, the virtual fitness partner depicts a famous athlete, friend, or other actual person, and the form, style, or other characterizations of the physical motions of the virtual fitness partner is determined based on the form, style, or other characterization of physical motions made by the actual person when performing the fitness activity.

In some embodiments, the appearance data of the virtual fitness partner is depicted differently in accordance with the pace of the partner velocity vector of the virtual fitness partner. For example, the step stride and/or stride distance depicted in the display of a jogging, running, and/or hiking virtual fitness partner can increase and decrease as the pace of the partner velocity vector increases and decreases, respectively. Similarly, RPM and/or cadence depicted in the display of a biking virtual fitness partner; stroke rate or size of splashes depicted in the display of a swimming virtual fitness partner; and/or other visual features of depiction of performance of the fitness activity that indicate pace can increase and decrease as the pace of the partner velocity vector increases and decreases, respectively. Sweat, perspiration, and/or redness of face of the virtual fitness partner displayed, and/or a heaviness of breathing or a breathing rate of the virtual fitness partner generated as audio data and played through the speakers, can also increase and/or decrease with a corresponding increase and/or decrease of pace of the virtual fitness partner, and/or can increase over time, for example, when the length of the fitness activity exceeds a threshold. These features can also increase or decrease as biometric data of the user indicates increasing and/or decreasing heart rate, breath rate, and/or effort put forth by the user. Some or all of these effects can be based on transit velocity and/or biometric data corresponding to the user, and can change in response to detecting event trigger conditions.

In various embodiments, the fitness partner profile data can include fitness partner profiles corresponding to a plurality of virtual fitness partners. This can include different appearance data, partner velocity data, and/or event triggering conditions. In such examples, a plurality of virtual fitness partners can each be associated with overlapping and/or non-overlapping pace ranges. For example, pace can be quantized into a plurality of pace levels, and each level can map to one of the plurality of virtual fitness partners. The appearance data corresponding to each virtual fitness partner can be based on the pace level, for example, with appearance data that depicts progressively slower virtual fitness partners at progressively slower pace levels. For example, a highest one of the plurality of pace levels can correspond to appearance data depicting an Olympic athlete and/or famous athlete. The next highest one of the plurality of pace levels can correspond to appearance data depicting to a strong-looking and/or fit-looking person. Progressively lower ones of the plurality of pace levels can depict a kid on a bicycle, a heavy-set fellow, a heavy-set lady, a little kid jogging, three ladies on their morning walk, a man in a wheel chair, an old lady with a cane and/or, finally, a toddler running loose.

The virtual fitness partner currently displayed can be determined by quantizing the pace indicated by the transit velocity vector into one of the plurality of pace levels, and displaying the corresponding one of the plurality of virtual fitness partners traveling at a corresponding pace. As the user's pace changes enough to be categorized in to a new pace level, this can trigger one of the plurality of event conditions to indicate a change in the appearance data displayed in accordance with the virtual fitness partner of the new pace level, and to indicate a change in the pace of the virtual fitness partner in accordance with the new pace level. In some embodiments, the virtual fitness partner can undergo a change in appearance between different ones of the plurality of fitness partners in response to one or more of the plurality of event trigger conditions.

In other embodiments, a plurality of fitness partners can be depicted to perform the fitness activity with the user. Multiple fitness partners can be displayed simultaneously within the display region, traveling in accordance with their own partner velocity data. In some embodiments, the plurality of fitness partners each travel in accordance with their own partner velocity data, which can be dictated by the plurality of quantized pace levels. As the user slows down, virtual fitness partners with higher paces can be depicted to pass the user in accordance with their partner velocity data and their relative velocity with respect to the user, and virtual fitness partners with slower paces can come into view from behind. Similarly, as the user speeds up, virtual fitness partners with slower paces can be passed and disappear from view by the user, and virtual fitness partners with higher paces can be depicted to emerge into view from ahead.

The breakdown of quantized pace levels and/or paces indicated in the partner velocity data can be configured by the user based on their fitness goals, can be configured based on average user pace and/or personal best data determined by the eyewear processing system 150 based on motion log 212 corresponding to prior transit data of the user, and/or can otherwise be determined. The appearance data for the quantized pace levels can also be configured by the user, for example, where the appearance data for each level is selected from a set of options. In some embodiments, the user can select their own appearance data for one or more fitness partners of the plurality of virtual fitness partners, for example, where the user uploads a picture of their heavy-set boss to generate appearance data for a lower quantized pace level, and/or uploads a picture of their fitness idol to generate appearance data for a higher quantized pace level. The appearance data and/or partner velocity data for some or all of the quantized pace levels can be determined based on user profile data of other users of the system, such as friends of the user or famous athletes.

In some embodiments, the display data can include other features and/or objects for display to the user, superimposed upon the physical surroundings. This can include visual indications of navigation data and/or route hazards for display to the user. In embodiments where the user is performing an activity indoors, such as on a treadmill, on an indoor track, or otherwise in a location that isn't picturesque, the display data can simulate more ideal surroundings by displaying an outdoor path corresponding to the transit route of the user, trees along the transit path, a blue sky above the horizon of the surface of the transit, nature features, and/or other simulated environmental surroundings. In particular, in embodiments where the user is utilizing stationary workout equipment, such embodiments may be preferred to simulate a more natural experience in a setting where the user does not need complete awareness of their actual physical surroundings.

Figure 3A:
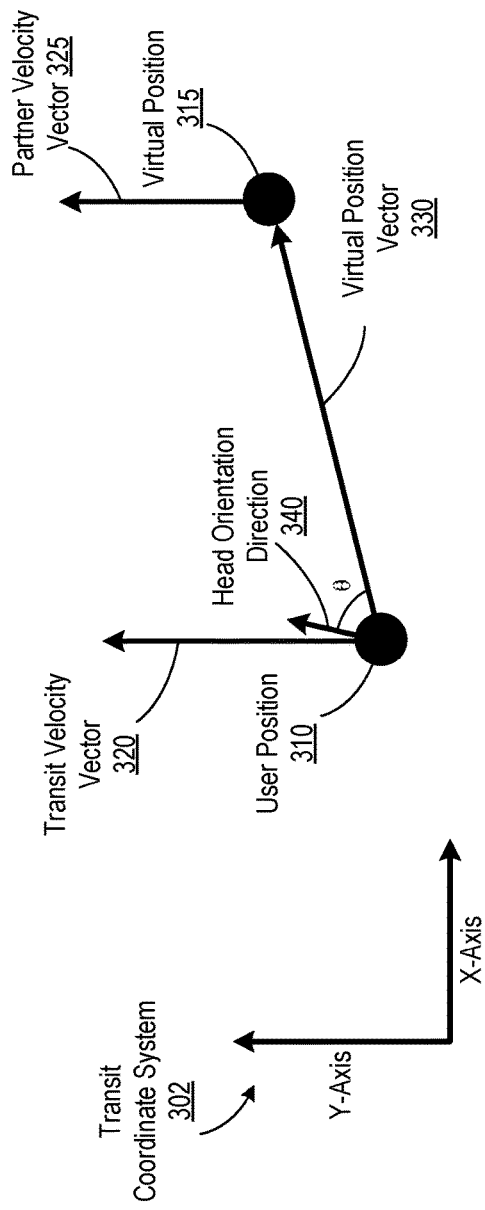
FIG. 3A is a diagram that illustrates the relationship between a user position, a transit velocity vector, a virtual position vector, a partner velocity vector, and a head orientation direction in accordance with various embodiments of the present invention.
Figure 3B:
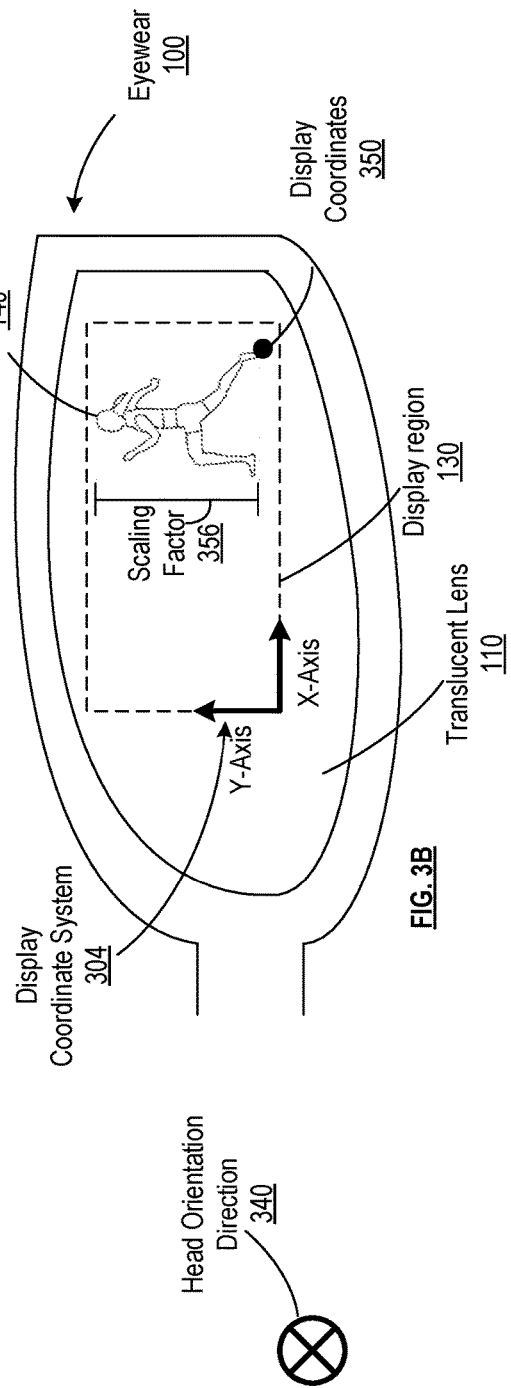
FIG. 3B is a graphical illustration of a display device, demonstrating the relationship between the virtual position vector and the head orientation direction of FIG. 3A, and display coordinates of a virtual fitness partner in accordance with various embodiments of the present invention.
Figure 3C:
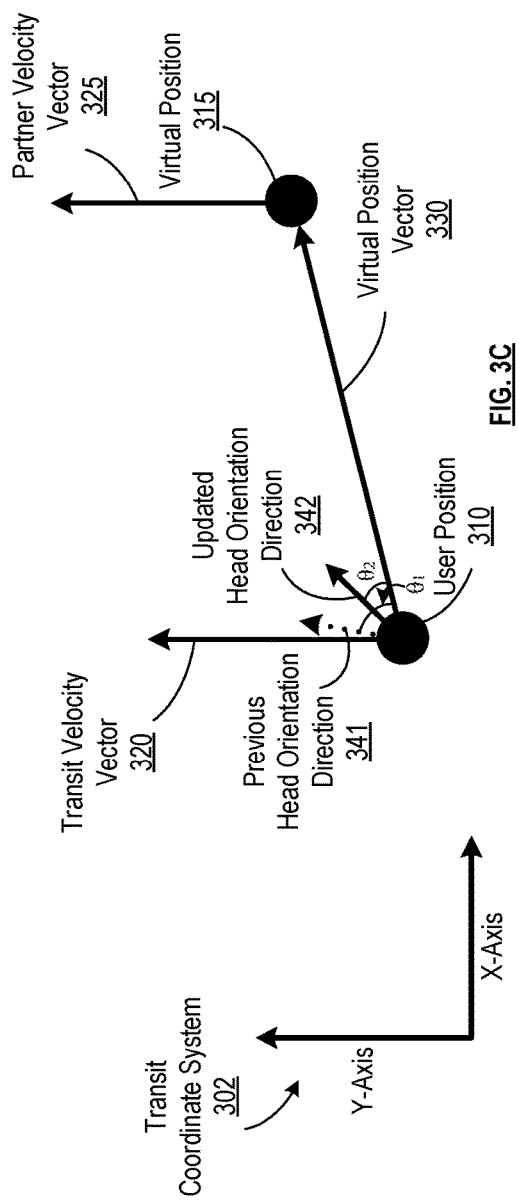
FIG. 3C is a diagram that illustrates the relationship between a user position, a transit velocity vector, a virtual position vector, a partner velocity vector, and a head orientation direction in accordance with various embodiments of the present invention.
Figure 3D:
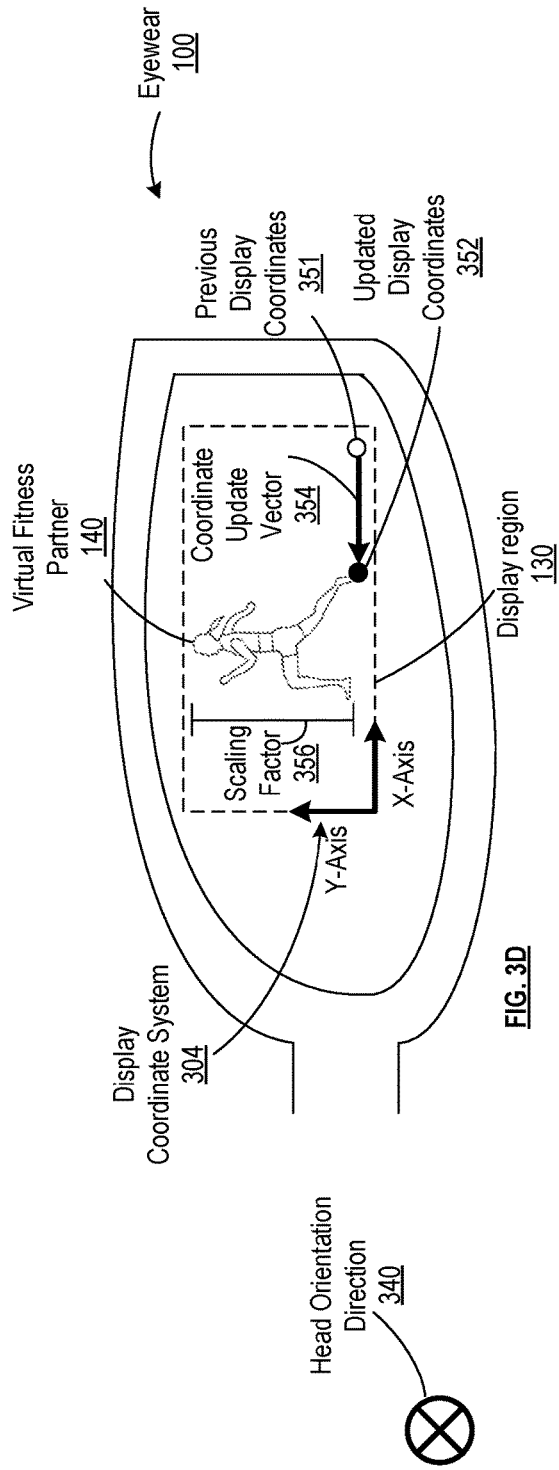
FIG. 3D is a graphical illustration of a display device, demonstrating the relationship between virtual position vector and the head orientation direction of FIG. 3C, and display coordinates of a virtual fitness partner in accordance with various embodiments of the present invention.

FIGS. 3A, 3C, and 3E include diagrams that illustrate the relationship between the user position, the transit velocity vector, the virtual position vector, and the partner velocity vector. Corresponding FIGS. 3B, 3D, and 3F, accordingly, include graphical illustrations that show the relationship between virtual position vector, the head orientation vector, display coordinates of the virtual fitness partner within the display region, and the scaling factor.

FIG. 3A includes a user position 310 and a transit velocity vector 320 associated with the user. The transit velocity vector 320 can be determined by the motion data generated by the eyewear processing system 150 based on sensor data collected by the motion sensors 260, for example, by calculating displacement of the user over a time interval. The y-axis of the transit coordinate system 302 can be dictated based on the transit direction of transit velocity vector 320.

While not depicted in FIG. 3A, the transit coordinate system 302 can have an origin point corresponding to the user position 310. The user position can be considered as an anchor point in the system, where the virtual position 315 of the virtual fitness partner is relative to the user position 310. Thus, the virtual position 315 of the virtual fitness partner 140 can be represented by a virtual position vector 330, indicating the distance of virtual position 315 from the user and the direction of virtual position 315 from the user. The transit of the virtual fitness partner can be characterized by a partner velocity vector 325, which indicates a virtual pace of the transit and a virtual direction of the transit.

The partner velocity vector 325 can be predetermined, for example, based on the fitness partner profile data. For example, the fitness partner profile data can indicate a constant, set pace at which the virtual fitness partner will always perform the fitness activity. For example, the fitness partner profile data 216 can indicate that the virtual fitness partner will jog at a constant rate in accordance with a 7 minute-mile, bike at a constant speed of 10 miles per hour, etc. The fitness partner profile data can indicate preset changes in pace in preset intervals at which the virtual fitness partner will perform the fitness activity. For example, the fitness partner profile data could indicate that the virtual fitness partner bike at 15 miles per hour for the first 10 minutes, at 12 miles per hour for the next 30 minutes, at 16 miles per hour of the next 5 minutes, and at 7 miles per hour for the last 10 minutes. The preset pacing intervals can be selected or otherwise configured by the user based on training goals, and/can be generated by the eyewear processing system based on elevation data or other data corresponding to a predetermined route of the fitness activity.

The fitness partner profile data 216 can be also be preset based on a motion log 212 of a prior transit of the user associated with the eyewear processing system 150, a prior transit of a different user of the system, or a simulated prior transit. Thus, the fitness partner profile data can include a plurality of timestamped partner velocity vectors, at intervals corresponding to a collection rate of the corresponding motion sensors 260, and the virtual fitness partner can perform the fitness activity in accordance with the plurality of timestamped partner velocity vectors. For example, the fitness partner profile data can be preset such that the virtual fitness partner performs the fitness activity in accordance with a most recent prior transit of the user, of a prior transit of a friend of the user, of a prior transit corresponding to a predetermined route of the current transit, a personal best transit, and/or of a prior transit of a famous athlete. The prior transit used in the fitness partner profile data can be determined by the eyewear processing system 150 automatically and/or can be selected by the user. In some embodiments, both the pace and direction of the plurality of timestamped partner velocity vectors is used to dictate the pace and direction of the virtual fitness partner. In some embodiments, only the pace of the plurality of timestamped partner velocity is used, and thus only the pace of the virtual fitness partner is predetermined.

Rather than dictating the partner velocity vector directly in the fitness partner profile data 216, the fitness partner profile data can indicate other information used to determine the transit velocity vector in real-time. For example, the fitness partner profile data can indicate a predetermined virtual position vector, for example, to ensure that the virtual fitness partner always remain in a constant virtual position relative to the user. In this fashion, as the user speeds up, slows down, and/or changes direction, the virtual fitness partner will follow suit to remain in the same virtual position. Thus, the partner velocity vector will be determined in real-time as a function of the transit velocity vector and preconfigured virtual position vector data. Such embodiments can be used in conjunction with the example discussed in FIG. 3G or other embodiments where the pace and/or direction of the virtual velocity vector is dictated by changes in the transit velocity vector, such that the virtual fitness partner follows the user's pace and/or route in real-time based on the motion data.

In such embodiments, the user can configure the x-component and y-component of the virtual position vector, in accordance with their preferences. As described herein, the x-component and y-component of the virtual position vector are with respect to the transit coordinate system 302, where the y-axis is dictated by the transit direction of the user, and where the user position 310 is the origin (0,0) of the transit coordinate system. If the user prefers to follow behind a fitness partner, the y-component of the virtual position vector can be set to a positive magnitude, where the magnitude is further dictated by how far behind the user wishes to lag behind their virtual fitness partner. Meanwhile, for a user that prefers to run directly alongside their virtual fitness partner, the y-component of the virtual position vector can be set to zero, or to a much smaller magnitude. Some users may wish for their virtual fitness partner to lag slightly behind, and the y-component of the virtual position vector can be set to a negative magnitude accordingly. In such embodiments, the virtual fitness partner may only be displayed to the user when the user turns their head in a direction towards the virtual fitness partner.

Similarly, the x-component of the virtual position vector can be set based on user preferences. For example, the user can dictate if they wish for their virtual running partner to run to their right or their left, and the x-component of the virtual position vector can be set to a positive or a negative value, respectively. The user can further designate an offset in the x-direction, which can dictate the magnitude of the x-component of the virtual position vector. The user may prefer to designate the total distance from the fitness partner, designating the magnitude of the virtual position vector, and the magnitude of the x-component can be determined given the configured magnitude of the y-component and the configured magnitude of the virtual position vector.

In embodiments that use predetermined partner velocity vector data, an initial virtual position vector, dictating the initial position of the virtual fitness partner with respect to the user, can still be configured. For example, if the user's goal is to keep pace with their virtual fitness partner and its predetermined partner velocity vector data throughout the transit, and thus attempt to keep the virtual position vector fixed throughout the transit, the x-component and y-component can be set similarly based on user preferences. The initial virtual position vector can also be based on other configuration data and/or can otherwise be determined by the eyewear processing system 150.

The x-component of an initial and/or predetermined virtual position vector can be determined based on known a known width of path corresponding to a predetermined route and/or corresponding to the current location of the user identified in the location data. For example, the known width can correspond to a footpath, road, trail, track, swimming lane, or other designated surface on which the user performs the fitness activity. The path width can be entered by the user, can be determined based on the image data, can be determined based on the location data and map data indicating a path features of a path within the vicinity of the user, and/or can be retrieved from the eyewear server system 295 and/or the Internet. In some embodiments, the user can enter their preferred location along the path relative to the path width, and the x-component can be set such that the virtual fitness partner runs within the path, for example, by determining the distance from the preferred user location to the edge of the path, along the width axis of the path, where the virtual running partner is depicted to run along the edge of the path.

As a user may deviate from their designated path position during transit, the x-component of the fitness partner velocity vector can instead be determined in real-time as a function of the position of the user along the width of the path and/or a distance of the user from the path boundary. For example, this can be determined based on the object recognition performed by the eyewear processing system on the image data to detect path features, such as the edge and/or the width of the path as discussed herein. Alternatively, the location data and corresponding map data can indicate the features such as the width of the path a user is detected to be on, and the position of the user along the path width axis. The user can set, or the fitness partner profile data can otherwise designate, a fixed path offset value of the virtual fitness partner position from the edge of the path. For example, if the virtual fitness partner is designated to run on the right side of the user, and if the user is following the direction of the path orthogonal to the width axis of the path, the magnitude of the x-component of the fitness partner position vector can be determined by calculating a distance of the user position 310 to the edge of the path along the width axis of the path based on the image data, and by then subtracting the path offset value from the determined distance, where the difference sets the magnitude of the x-component of the fitness partner position vector. In some embodiments, the fitness partner velocity vector will be determined to ensure that the virtual fitness partner says on the path, and moves in the direction of the path.

In some embodiments, the fitness partner profile data will include predetermined partner velocity vector data that is associated with navigation data. For example, the predetermined virtual velocity data may be a set of unit vectors that are location-tagged, to indicate the direction of travel at each location along the route, and/or can include other navigation data. Such data can be configured to follow the exact prior route of a prior transit collected via location data associated with the motion log data. This can also be determined based on a route selected by the user on a map interface and/or from a set of known transit routes. This can also be determined based on a known route that compared favorably to the user's current location indicated in the location data. Here, the fitness partner profile data can further include the predetermined position vector data with a positive y-component, and thus the virtual fitness partner can be configured to lead the user along a predetermined route, but at a pace dictated by the transit velocity vector of the user. This can be useful in embodiments where the user does not wish to consult navigation data along the route, and can instead rely on following their virtual fitness partner. This can also be useful in embodiments where the route is not obvious and/or not clearly marked, such as a hiking trail, where the user can again rely on following their virtual fitness partner.

In some embodiments, the fitness partner profile data can further include pace threshold data, such as a maximum pace and a minimum pace. For example, if the virtual fitness partner is configured to match the pace of the user but the minimum pace is set to 2 miles per hour, the virtual fitness partner will reduce its pace to 2 miles per hour if the user stops, and will continue moving away from the user. If the maximum pace is set to 5 miles per hour and the user begins running at 5.5 miles per hour, the user may pass the virtual fitness partner.

The fitness partner profile data can include a pace differential window, for example, designating the range of pace differential from the user's transit pace if the virtual fitness partner is configured to match the pace of the user. In such embodiments, the pace of the virtual transit velocity can deviate within the pace differential window, relative to the user transit pace, randomly and/or pseudo-randomly to simulate a more natural running partner. Similarly, a direction differential window can be indicated in the fitness partner profile data, designating the range of direction differential from the user's transit direction if the virtual fitness partner is configured to match the pace of the user.

In embodiments where the virtual fitness partner is configured to match continuous and/or varying partner velocity vector that is predetermined, a pace differential window and/or direction differential window relative to the predetermined partner velocity vector can similarly be indicated in the fitness partner profile data, and the pace and/or direction of the virtual transit velocity can deviate within the pace and/or direction differential windows, relative to the predetermined partner velocity vector at a particular time, randomly and/or pseudo-randomly to simulate a more natural running partner. The pace differential window and/or direction differential windows can be preconfigured, can be configured by the user, and/or can be otherwise determined by the eyewear processing system 150.

Alternatively or in addition, a position differential window, can be set and can include, for example, with respect to an x-component window, a y-component window, and/or a vector magnitude window. The virtual position vector can be configured to remain within range of the position differential window, and the pace and/or direction of the partner velocity vector can be determined to keep the position of the virtual fitness partner within the position differential window, and can allow the position of the virtual fitness partner to deviate randomly and/or pseudo-randomly within the position differential window.

Alternatively or in addition, the fitness partner profile data can include path offset windows that dictate where along the width axis of the path, and/or where outside the path along the width axis, the virtual fitness partner can move, based on preconfigured path information, based on location data and map data that indicate the path width and user location along the width axis of the path, and/or based on detecting the edge of the path by processing the image data. The virtual fitness partner can move within the area designated by the path offset window randomly and/or pseudo-randomly to simulate a more natural running partner, and the virtual position vector and/or partner velocity vector can be adjusted accordingly to ensure the virtual fitness partner remains within the path offset window.

One of the plurality of event trigger conditions can include determining that a magnitude of a scalar projection of the virtual position vector onto a vector corresponding to the transit direction exceeds a lag threshold, for example, as indicated by the y-component window of the position differential window. The lag threshold can be predetermined, can be configured by the user, and/or can be indicated in the fitness partner profile data. The corresponding one of the plurality of fitness partner actions can include changing a magnitude of the partner velocity vector from a first pace to a second pace that is slower than the first pace. In various embodiments, a second one of the plurality of event trigger conditions includes determining that the magnitude of the scalar projection of the virtual position vector onto the vector corresponding to the transit direction no longer exceeds the lag threshold, and the corresponding one of the plurality of fitness partner actions includes resetting the magnitude of the partner velocity vector to the first pace.

One of the plurality of event trigger conditions can include determining that a magnitude of a scalar projection of the virtual position vector onto a vector that is orthogonal to the transit direction exceeds a gap threshold, for example, as indicated by the x-component window of the position differential window. The gap threshold can be predetermined, can be configured by the user, and/or can be indicated in the fitness partner profile data. The corresponding one of the plurality of fitness partner actions includes setting a first updated direction to generate a first updated partner velocity vector, wherein the magnitude of a first cross product of the first updated partner velocity vector and the transit velocity vector is nonzero. A second one of the plurality of event trigger conditions can include determining that the magnitude of the scalar projection of the virtual position vector onto the vector that is orthogonal to the transit direction no longer exceeds the gap threshold. A second one of the plurality of fitness partner actions corresponding to the second one of the plurality of event trigger conditions can include setting a second updated direction to generate a second updated partner velocity vector, where the magnitude of a second cross product of the second updated partner velocity vector and the transit velocity vector is less than the magnitude of the first cross product.

In some embodiments, one of the plurality of event trigger conditions includes detecting a change in transit direction from a first direction to a second direction, and the corresponding one of the plurality of fitness partner actions includes setting an updated direction of the partner velocity vector in accordance with the change in transit direction. This can be utilized when the virtual position vector and/or position differential window is predetermined to cause the virtual fitness partner to follow the direction changes of the user.

In some embodiments, the one of the plurality of event trigger conditions includes determining that a direction of vector projection of the virtual position vector onto a vector corresponding to the transit direction is opposite the transit direction, for example, indicating the fitness partner is behind the user and/or indicating the user has passed the fitness partner. In some embodiments, the partner velocity vector will increase in response, for example, induced by the pace differential window and/or the y-component window of the position differential window, and can cause the virtual fitness partner to pass the user. In some embodiments, the virtual fitness partner may be visually and/or audibly depicted to congratulate the user and/or otherwise acknowledge that the user has passed the virtual fitness partner.

A plurality of modes of operation can be indicated in the fitness partner profile data, including some or all of the embodiments discussed herein. In response to determining one or more of the plurality of event trigger conditions has occurred, the eyewear processing system 150 can change from a first mode to a second mode. Event trigger conditions that induce mode changes can include user command data collected as voice command data to the microphone 268 and/or gesture command data collected by the motion sensor 260 and/or image sensor 262. Event trigger conditions that cause mode changes can also be based on the transit velocity vector, for example, in response to determining a user has stopped or drastically changed their pace, and/or can be based on any event trigger conditions discussed herein.

For example, in a first mode, the virtual fitness partner can perform the fitness activity in accordance with predetermined partner velocity vector data as previously discussed, for example, following motion log data from a prior activity. In response to detecting that the user has lagged behind the virtual fitness partner more than a threshold amount, or passed ahead of the virtual fitness partner more than a threshold amount, the eyewear processing system 150 can change to a second mode, for example, where the virtual fitness partner moves in accordance with predetermined virtual position vector data to match the pace of the user and keep the virtual fitness partner in view. If the user's pace compares favorably to a threshold indicating they resumed their prior transit pace or an otherwise favorable transit pace, the eyewear processing system 150 can change back to the first mode, and the fitness partner can resume moving in accordance with the virtual velocity data.

In some embodiments, a mode can include a pause mode selected by the eyewear processing system in response to determining the user has stopped, for example, to tie their shoe or take a drink, or in response to user command data selecting the pause mode. If the virtual fitness partner is following a timestamped motion log, the virtual fitness partner can pause its transit and resume when the pause mode has ended based on a predetermined time elapsing, determining the user has begun moving again, and/or in response to user command data selecting to end the pause mode. Timestamped motion log data corresponding to the current transit can also pause during the pause mode, and resume again once the pause period has elapsed, such that the pause period is not indicated in the motion log data.

FIG. 3A also illustrates a head orientation direction 340, based on the head orientation collected in the motion data, relative to the direction of the transit velocity vector. For example, if the user is running or otherwise undergoing transit while upright, along a flat surface, the head orientation direction 340 represents side-to-side head turns, and/or the projection of head turns along the plane parallel to the surface. For the purposes of the discussion of FIGS. 3A-3G, such embodiments will be considered, where head orientation direction 340 is on, and/or is projected upon, the transit coordinate system 302. However, in other activities, such as climbing or swimming, the head orientation direction may be with respect to a different plane, discussed in further detail in the discussion of FIGS. 3J-3L.

FIG. 3B illustrates the display of virtual fitness partner 140 within the display region 130, in accordance with the head orientation direction 340 and the virtual position vector 330. As shown, the head orientation direction 340 is pointing into the page, and thus this illustration represents the view of the user through the translucent lens. Here, the virtual position 315 of the virtual fitness partner, with respect to the head orientation direction 340, is ahead and to the right. This information is used to determine a scaling factor 356, dictating a size at which the virtual fitness partner 140 is displayed within the display region; and display coordinates 350, in accordance with a display coordinate system 304 determined based on the display region 130, the display device 120, and/or the translucent lens 110. As shown, the virtual fitness partner is displayed on a translucent lens 110 corresponding to the user's right eye, depicted to be running alongside the user's right side. While only the right eye is shown, during the activity the virtual fitness partner may be depicted to run in the center of the user's transit path and/or on the left side of the user, and the virtual fitness partner can be displayed in a display region on a translucent lens 110 corresponding to the user's left eye accordingly, and/or can be displayed for view by both eyes.

While the scaling factor is shown with respect to the y-axis of the display coordinate system 304, any scaling factor and/or size data can be used to determine the size at which the virtual fitness partner 140 is displayed. Similarly, while the display coordinates 350 is shown anchored at the bottom right of the image of the virtual fitness partner, the display coordinate data can correspond to any coordinates used to depict the position of the fitness partner, and can include a plurality of dynamic coordinates corresponding to the virtual fitness partner, such as coordinates along the arms and legs that independently change with respect to the virtual fitness partner's position to depict the motion of the virtual fitness partner in accordance with virtual performance of the fitness activity and/or in accordance with one or more fitness partner actions.

As discussed previously, 360-degree view data of the virtual fitness partner that dictates which of a plurality of two dimensional views of the virtual fitness partner is depicted can also be determined and displayed accordingly. The displayed one of the plurality of two dimensional views can be selected as a function of head orientation direction 340 and direction of partner velocity vector 325. In stereoscopic systems, display coordinates 350, scaling factor 356, and 360-degree view data can be calculated separately for two separate display regions 130 corresponding to each eye, and can each correspond to different values for each eye. This is discussed in further detail in the discussion of FIGS. 3H-3I.

The display coordinates 350 can be a function of $\theta$, the angle from the head orientation direction 340 to the virtual position vector 330. In particular, the x-coordinate of the display coordinates 350 with respect to the x-axis of the display coordinate system 304 can be an increasing function of the magnitude of $\theta$, if the center of the user's field of view with respect to the x-axis corresponds to the origin of the display coordinate system 304, and/or if the y-axis of the display coordinate system 304 is the closest axis of the display region to the center of the user's field of view, with respect to the x-axis. If $\theta$ is zero, the virtual fitness partner should be centered in the user's field of view with respect to the x-axis. The sign of $\theta$ can dictate whether the virtual fitness partner is on the left or right portion of the user's field of view, and thus whether the virtual fitness partner is displayed to the left or the right eye can be a function of the sign of $\theta$. The magnitude of $\theta$ can dictate how centered the virtual fitness partner is in the user's field of view, and whether the virtual fitness partner is displayed to both eyes can be a function of the magnitude of $\theta$. If the magnitude of $\theta$ is too large, the virtual fitness partner may not be displayed at all, or only a portion of the virtual fitness partner may be displayed, for example, indicating that the virtual fitness partner is outside of the user's field of view.

In some embodiments, the value of $\theta$ and/or the value of the x-coordinate of the display coordinates 350 can be used to determine whether the user is looking at the virtual fitness partner 140. For example, the eyewear processing system 150 can compare the magnitude of $\theta$ and/or value of the x-coordinate of the display coordinates 350 to a configured threshold value, where an event trigger condition corresponding to the user looking at the virtual fitness partner 140 is determined to be true when $\theta$ and/or value of the x-coordinate of the display coordinates 350 compared favorably to the configured threshold value. As another example, the derivative of $\theta$ with respect to time can be used to determine if the user made a sharp, deliberate turn towards their virtual fitness partner. Thus, the eyewear processing system 150 can further compare the derivative of $\theta$ with respect to time to a threshold, and/or compare the difference of two values of $\theta$ calculated in immediate succession to a threshold. An event trigger condition corresponding to the user making a sharp head motion towards their virtual fitness partner is determined to be true when the derivative of $\theta$ with respect to time is higher than a configured threshold derivative value and when the magnitude of $\theta$ is lower than a threshold angle differential value.

The y-coordinate of the display coordinates 350 with respect to the y-axis of the display coordinate system 304 can be an increasing function of the magnitude of the virtual position vector to depict the distance of the virtual fitness partner from the user. Similarly, the scaling factor 356 can be a decreasing function of the magnitude of the virtual position vector.

Furthermore, as the user also nods their head up and/or down, the y-coordinate of the display coordinates 350 with respect to the y-axis of the display coordinate system 304 will change accordingly. The head orientation data can include a head nod direction with respect to the plane orthogonal to the x-axis. This plane will herein be referred to as the head nod plane, and corresponds to the plane at which a user nods their head up and down. A second angle $\phi$ can be calculated as the angle between the head orientation direction projected upon the head nod plane and the y-component of the virtual position vector. Thus, the y-coordinate of the display coordinates of the virtual fitness partner in the display region can further be a function of $\phi$. In some embodiments, the magnitude of $\phi$ and/or derivative of $\phi$ with respect to time can be used to determine event trigger conditions corresponding to the user nodding their head to look towards their virtual fitness partner, for example, by comparing one or both of these values to configured thresholds, and/or by comparing a head orientation dictated by both $\theta$ and $\phi$ to a configured threshold. The head nod plane and $\phi$ are discussed further in the discussion of FIGS. 3I-3J FIGS. 3C and 3D illustrate how the display of the virtual fitness partner can change with changes in head orientation direction 340. In FIG. 3C, the head orientation direction changes from previous head orientation direction 341 to updated head orientation direction 342. This, the virtual position 315 of the virtual position vector is has moved towards the center of the user's field of view. Accordingly, the coordinate update vector changes from previous display coordinates 351 to updated display coordinates 352 to display the virtual display partner closer to the center of the user's field of view. In particular, the coordinate update vector can be calculated as a function of difference $\theta_1 - \theta_2$, the angle from the previous head orientation direction 341 to the updated head orientation direction 342. For example, given the virtual position vector has remained constant, the magnitude of coordinate update vector can be a monotonically increasing function of $|\theta_1-\theta_2|$, and the direction of coordinate update vector 354 can be a function of the sign of $\theta_1-\theta_2$.

FIGS. 3E and 3F illustrate how the display of the virtual fitness partner can change with changes in the virtual position vector. For example, the virtual position vector can be a function of relative velocity with respect to the user, where relative velocity is calculated as a function of the transit velocity vector 320 and the partner velocity vector 325, such as the vector difference calculated by subtracting the partner velocity vector 325 from the transit velocity vector. Thus, a change in the relative velocity with respect to the user can induce a change in the virtual position vector. The change in the relative velocity with respect to the user can be induced by a change in the transit velocity vector, as shown in FIG. 3E, by a change in the virtual velocity vector, and/or by a change in the transit velocity vector and the virtual velocity vector. Note that a change in the transit velocity vector and/or the partner velocity vector can include a change in the respective pace, direction, or both. Changes in the transit velocity vector can be determined in the motion data by subtracting an updated transit velocity vector from a previous transit velocity vector and/or by calculating acceleration data in the motion data, for example, by computing the derivative of transit velocity with respect to time. Changes in the virtual velocity vector can be a function of changes in the virtual position vector, can be predetermined based on the fitness partner profile data, and/or can be a function of changes in the transit velocity vector, for example, in embodiments where the virtual position vector is constrained to be fixed and/or within a window Such calculations can be performed by the eyewear processing system 150 in real-time at a rate dictated by the collection rate of the corresponding at least one motion sensor 260.

FIGS. 3E and 3F illustrate and example showing how the change in user transit pace can affect the display of the virtual fitness partner. As shown in FIG. 3E, the magnitude of an updated transit velocity vector 322 decreased from the previous transit velocity vector 321, in response to detecting that the pace of the user slowed down based on the motion data. In response, the eyewear processing system 150 determines an updated virtual position vector 332 that is further away from the user position 310 with respect to the direction of transit as a result of an increased relative velocity of the virtual fitness partner in the direction of transit, calculated as a function of the updated transit velocity vector 322 and the partner velocity vector 325. The angle from the head orientation direction 340 to the virtual position vector also decreases from $\theta_1$ to $\theta_2$ as a result of the change in virtual position to from the previous virtual position 316 to the updated virtual position vector 317, where $\theta_1$ is the angle between the head orientation direction 340 and the previous virtual position vector 331 and $\theta_2$ is the angle between the head orientation direction 340 and the updated virtual position vector 332.

As shown in FIG. 3F, these changes induce changes in the scaling factor and display coordinates associated with the display of virtual fitness partner 140. As a result of an increase in the y-component of the virtual position vector in response to the decrease of user pace in the y-direction, the magnitude of the virtual position vector also increases. The increase in magnitude of the virtual position vector induces a decrease in the scaling factor from previous scaling factor 357 to updated scaling factor 358. The display coordinates also change from previous display coordinates 351 to updated display coordinates 352, represented by the coordinate update vector 354. The update coordinate vector can be calculated as a function of the change in θ and the change in the magnitude of the virtual position vector. In this example, as a result in the reduction of the magnitude of θ from $\theta_1$ to $\theta_2$, the x-coordinate of the display coordinates decreases to shift the virtual fitness partner towards the center of the user's field of view. As a result of the increase in the magnitude of the virtual position vector, the y-coordinate of the display coordinates increase to shift the virtual fitness partner upward.

FIG. 3G illustrates how changes in transit velocity data detected in the motion data can affect partner velocity data in some embodiments as discussed herein. For example, in response to determining the user has turned and begun transit in a new direction, the virtual fitness partner can also be updated to begin transit in this new direction, where their subsequent virtual positions 315 are determined based on the updated partner velocity vector. In particular, in response to determining the transit velocity vector has changed from a previous transit velocity vector 321 to an updated transit velocity vector 322 that induces a change in direction by an angle of α, the partner velocity vector can change from a previous velocity vector 326 to an updated velocity vector 327 at the same angle α and/or a similar angle. This can be used to simulate the virtual fitness partner following and/or running alongside the user, changing direction with the user's routing decisions. The display of the virtual running partner is still based on the head orientation direction, and thus may cause the head orientation direction to change by an angle of a as well, if the user's head is oriented in the same direction relative to the direction of transit during the change in transit direction.

FIGS. 3H-3I illustrate an example of how the displayed two dimensional view of the virtual fitness partner, presented within display region 130 of eyewear 100, can change. A displayed one of a plurality of two dimensional views can be selected as a function of head orientation direction 340, the direction of partner velocity vector 325, and the virtual position vector 330. FIG. 3H illustrates the presentation of the virtual fitness partner with respect to a first two dimensional view, and FIG. 3I illustrates presentation of the virtual fitness partner with respect to a second two dimensional view. Furthermore, FIGS. 3H and 3I illustrate the virtual fitness partner presented as a different avatar than that depicted in FIGS. 3B, 3D, and 3F. In some embodiments, as presented in FIGS. 3H and 3I, the avatar can be presented in the shape of an athlete performing the fitness activity, in a single color. Other embodiments can include other avatars and/or other appearance data, discussed herein, and any avatar corresponding to any appearance can be presented from multiple views.

FIG. 3H illustrates presentation of a virtual fitness partner at display coordinates 380 and scaling factor 386, which can be determined as discussed in FIGS. 3A-3G. Here, the virtual fitness partner is depicted at a first two dimensional view, corresponding to a side view of the virtual fitness partner. This selected two dimensional view of the virtual fitness partner is presented at display coordinates 380 with respect to display coordinate system 304, corresponding to a corner or peripheral portion of the user's view, to simulate the virtual fitness partner to be running alongside the user, in the same direction as the user, while the user is facing forward, where the head orientation direction 340 matches the direction of the transit velocity vector 320. In particular, the displayed side view of the virtual fitness partner can be selected deterministically from a plurality of views of the virtual fitness partner in response to determining the user is facing the transit direction, that the direction of the partner velocity vector matches the transit direction, and that the y-coordinate of the virtual position vector is small or equal to zero.

FIG. 3I illustrates an updated presentation of the virtual fitness partner 140 from the display presented in FIG. 3H. In particular, the virtual fitness partner moves from display coordinates 380 to updated display coordinates 382, characterized by the coordinate update vector 384. The scaling factor has also decreased to an updated scaling factor 388. These updates can be determined as discussed in FIGS. 3A-3G, and in particular as discussed in FIGS. 3E-3F. Furthermore, the virtual fitness partner is depicted at a second two dimensional view, corresponding to a back view of the virtual fitness partner. This selected two dimensional view of the virtual fitness partner, presented at updated display coordinates 382 corresponding to a more central portion of the user's view, can simulate the virtual fitness partner to be running ahead of the user, in the same direction as the user, while the user is facing forward, where the head orientation direction 340 matches the direction of the transit velocity vector 320. In particular, the displayed back view of the virtual fitness partner can be selected deterministically from a plurality of views of the virtual fitness partner in response to determining the user is facing the transit direction, that the direction of the partner velocity vector matches the transit direction, and that the y-coordinate of the virtual position vector is large or has otherwise increased from that of FIG. 3H. In other words, when the virtual fitness partner is depicted to be traveling in the same direction as the user, and when the virtual fitness partner is depicted to be further ahead of the user, for example, because the user has slowed down and the virtual fitness partner has maintained pace, the virtual fitness partner will shift towards the center of the users view, become smaller, and be presented from a back view to simulate that the fitness partner is further ahead of the user. In such embodiments, given constant head orientation and constant relative direction of transit between the user and virtual fitness partner, the selected one of the plurality of two dimensional views of the virtual fitness partner can be a direct function of the y-coordinate of the virtual position vector, characterizing the changes in relative pace between the user and the virtual fitness partner. In some embodiments, the two dimensional view can be further selected based on additional factors, and can change as a function of the change in these additional factors, where the additional factors include the head orientation direction and/or the direction of the relative velocity between the user and the virtual fitness partner.

FIGS. 3J-3L illustrates transit coordinate systems corresponding to performance of different fitness activities. Note that as discussed herein, the y-axis of the transit coordinate system 302 is always with respect to the direction of the user's transit, indicated by the transit velocity vector that is calculated or otherwise determined based on the motion data. However, the axis about which a user turns their head, depicted in FIGS. 3J-3L as head axis 305, can be a different axis, relative to the transit direction, based on the fitness activities. In particular, the head orientation direction 340 discussed with respect to FIGS. 3A, 3C, and 3E can be dictated with respect to the plane that orthogonal to head axis 305, regardless of the transit direction. This plane will herein be referred to as the head turn plane, orthogonal to the head nod plane, and corresponding to the plane at which a user turns their head from side-to-side. The orientation of head axis 305 can be determined based on the motion data, such as accelerometer data. The calculation of $\theta$ as discussed with respect to FIGS. 3A-3G can be based calculating head orientation direction 340 as a projection of the head orientation upon the head turn plane.

FIG. 3J shows an example where a user is jogging. This depiction can also be used to represent any activity where the user is oriented upright relative to the surface along which they are traveling. Thus, the head axis 305 is orthogonal to the transit coordinate system 302, and thus the head turn plane corresponds plane defined by transit coordinate system 302. Thus, as discussed with respect to FIGS. 3A, 3C, and 3E, the head orientation direction 340 is a vector projected upon the transit coordinate system 302.

FIG. 3K shows an example where a user is climbing. This depiction can also be used to represent any activity where the user is oriented horizontally relative to the surface along which they are traveling. Thus, the head axis is parallel to the y-axis of transit coordinate system 302.

Consider the example where the virtual fitness partner is depicted to climb alongside the user. Again, this is dictated by the x-component of the virtual position vector with respect to the x-axis of the transit coordinate system 302. The head orientation direction 340 can be determined with respect to the head turn plane: the plane orthogonal to the head axis 305, which includes the x-axis. Thus, $\theta$ can be calculated as the angle between the projection of the virtual position vector upon the head turn plane and the head orientation direction 340, and the x-coordinate of the display coordinates of the virtual fitness partner in the display region with respect to display coordinate system 304 can still be a function of $\theta$. As the user turns their head towards their virtual climbing partner along the head turn plane, decreasing the magnitude of $\theta$, the virtual climbing partner moves towards the center of the user's field of view with respect to the x-axis of the display coordinate system 304.

However, consider the example where the position of the virtual fitness partner also has a y-component and is thus higher up the climbing surface than the user. The head nod plane becomes more important, as the user nods their head up and/or down to move a virtual fitness partner that is above or below them in and out of their field of view. $\phi$ can again be calculated as the angle between the head orientation direction projected upon the head nod plane and the y-component of the virtual position vector. The y-coordinate of the display coordinates of the virtual fitness partner in the display region can thus still be a function of $\phi$. As the user orients their head towards their virtual climbing partner along the head nod plane, decreasing the magnitude of $\phi$, the virtual climbing partner moves towards the center of the user's field of view with respect to the y-axis of the display coordinate system 304. If the user's head orientation is straight ahead, a climber with a virtual position too far above or below the user will not be in view and thus not be displayed.

In such embodiments, the value of $\phi$ and/or the value of the y-coordinate of the display coordinates 350 can be used to determine whether the user is looking at the virtual fitness partner 140. For example, the eyewear processing system 150 can compare the magnitude of $\phi$ and/or value of the y-coordinate of the display coordinates 350 to a configured threshold value, where an event trigger condition corresponding to the user looking at the virtual fitness partner 140 is determined to be true when $\phi$ and/or value of the y-coordinate of the display coordinates 350 compared favorably to the configured threshold value. As another example, the derivative of $\phi$ with respect to time can be used to determine if the user made a sharp, deliberate turn towards their virtual fitness partner. Thus, the eyewear processing system 150 can further compare the derivative of $\phi$ with respect to time to a threshold, and/or compare the difference of two values of $\phi$ calculated in immediate succession to a threshold. An event trigger condition corresponding to the user making a sharp head motion towards their virtual fitness partner is determined to be true when the derivative of $\phi$ with respect to time is higher than a configured threshold derivative value and when the magnitude of $\phi$ is lower than a threshold angle differential value.

The head orientation data determined in the motion data can include a head orientation vector that includes a head turn vector component, calculated as a projection of the head orientation vector on the head turn plane, and a head nod vector component, calculated as a projection of the head nod orientation vector on the head nod plane. Even in embodiments where the transit direction is not orthogonal to either of these planes, the virtual position vector can be projected upon the head nod plane and the head turn plane, $\theta$ and $\phi$ can be calculated accordingly, and the display coordinates of the virtual fitness partner can be determined as a function of $\theta$ and $\phi$.

FIG. 3L illustrates an example where a user is swimming. Since the y-axis of the transit coordinate system 302 is again parallel to the head axis, a virtual swimming partner swimming alongside, for example in an adjacent lane and/or ahead of the user, for example, along the same lane, and/or a combination of both, can be represented as a virtual position vector with x-components and y-components on the transit coordinate system accordingly. The head orientation vector can again be projected on the head turn plane and the head nod plane to determine a head turn vector component and a head nod vector component, respectively. The display coordinates of the virtual fitness partner can be determined as a function of $\theta$ and $\phi$, calculated as discussed with respect to FIG. 3K.

However, this assumes that the virtual swimming partner also be swimming on the surface of the water. In some embodiments, the virtual swimming partner can be depicted to swim below the user, such that a user swimming on the surface of the water sees their virtual swimming partner swimming below them in the same direction. This may be ideal as it does not require the user to turn their head while swimming, or induce the complications of superimposing the image of a swimmer splashing along the surface of the water, while still providing a pacing partner or otherwise motivational partner for the user. Thus, the consideration of depth is required, and a new dimension must be added to the system. Alternatively or in addition, if the user is snorkeling, diving, or otherwise swimming at varying depths, the consideration of depth is again required, where the virtual fitness partner can be depicted to swim at depths above or below the depth of the user.

In such embodiments, or other embodiments that require the consideration of the transit velocity vector, the partner velocity vector, and/or the virtual position vector in three dimensions, the transit coordinate system 302 can further include a z-axis. The transit velocity vector, the partner velocity vector, and/or the virtual position vector can thus be represented with an x-component, a y-component, and a z-component. The virtual position vector and the head orientation vector can be projected upon the head turn plane and the head nod plane, and these vector projections can thus be used to calculate $\theta$ and $\phi$, respectively, where display coordinates of the virtual fitness partner can be determined as a function of $\theta$ and $\phi$. The scaling factor can still be a decreasing function of the magnitude of the virtual position vector. In particular, as the magnitude of the z-component of the virtual position vector increases, for example, if the depth between the user and the virtual fitness partner increases, the magnitude of the virtual position vector will thus increase, and the scaling factor will decrease.

In some embodiments, for example, where a user is swimming laps in a pool and their virtual fitness partner is depicted to swim alongside them, the partner velocity vector will change direction when the virtual fitness partner reaches the edge of the pool, for example, depicting the virtual fitness partner flip turning or otherwise changing direction at the wall of the pool to begin swimming in the opposite direction. The edge of the pool can be determined in the image data and/or can be determined based on detecting the position where the user changes direction, indicating the user has reached the edge of the pool and begun swimming the opposite way down their lane. In response to detecting the change in direction of the user, the virtual fitness partner can be displayed on the opposite side of the display region and/or can displayed by a display region corresponding to the opposite eye, and/or otherwise displayed to depict that a virtual swimming partner has switched from being on the user's right side to the user's left side in response to the user changing directions.

Figure 4:
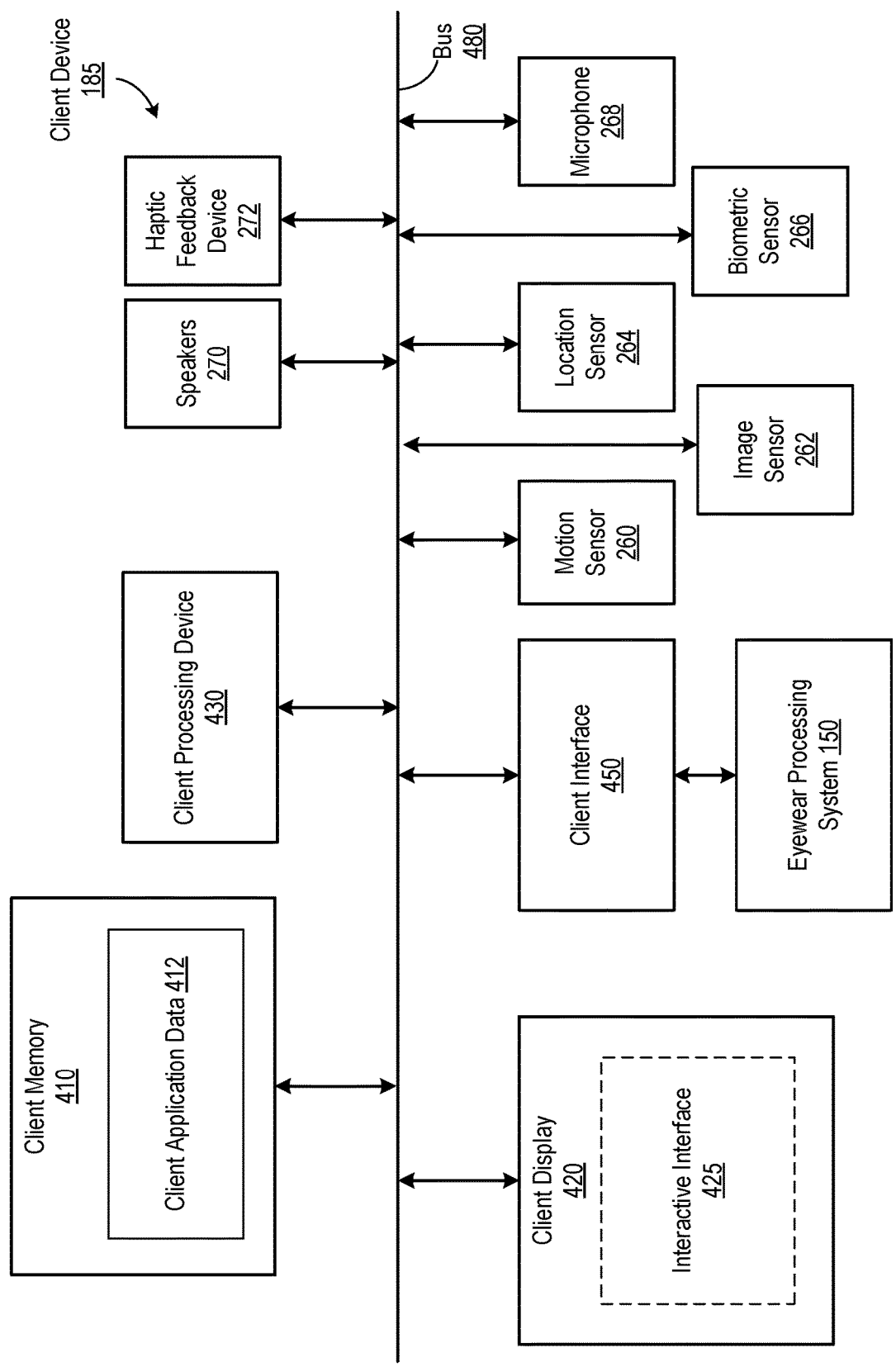
FIG. 4 is schematic block diagram of a client device in accordance with various embodiments of the present invention.

FIG. 4 presents a block diagram of a client device 185 in accordance with various embodiments of the present invention. The client device can include at least one client memory 410 and at least one client processing device 430, communicating via bus 480. The client processing device 430 can store client application data 412 and/or operational instructions that, when executed by the at least one client processing device 430, causes the at least one client processing device 430 to display an interactive interface 425 on a client display 420 in accordance with the client application data 412 and/or user input to the interactive interface 425. The client device 185 can generate application data such as configuration data, fitness partner profile data 216, and/or user profile data based on input the interactive interface for transmission to the eyewear processing system 150 and/or a server such as eyewear server system 295 by utilizing client interface 450. Some or all of the client application data 412 can include motion log 212, event log 214, and/or other data received from the eyewear processing system 150, which can be processed and/or displayed via the interactive interface 425. The interactive interface displayed by the client device in accordance with application data is discussed further in conjunction with the discussion of FIGS. 6A-6F. The input data to the interactive interface can be generated based on user input to a touchscreen, keyboard, mouse, buttons of the client device, microphone such as microphone 268, gesture input to motion sensor 260 and/or image sensor 262, and/or other user input devices associated with the client device 185.

In some embodiments, the off-board device 253 of FIG. 2 can be implemented utilizing the client device 185, and/or the application data can otherwise be sent to the eyewear processing system 150 by utilizing a short range wired and/or wireless communication protocol via client interface 450. In such embodiments, the client device can be worn and/or carried by the user during the fitness activity. The client device can include the at least one speaker 270 of FIG. 2 that generates sound in accordance with audio data received from the eyewear processing system 150 and/or the haptic feedback device 272 of FIG. 2 that generates haptic feedback in accordance with haptic feedback data received from the eyewear processing system 150. The client device 185 can include some or all of the sensors 260, 262, 264, 266, and/or 268, where the sensor data is sent to the eyewear processing system 150 for processing. Alternatively or in addition, some or all of the sensor data can be processed by the client device 185 to generate some or all of the motion data, fitness partner profile data, and/or some or all of the display data, which can then be transmitted to the eyewear processing system 150. In some embodiments, eyewear processing system 150 is integrated within the client device, for example, where the motion data generator 151 and/or fitness partner generator 152 of FIG. 1 are implemented by utilizing the client processing device 430 in accordance with execution of the client application data 412.

In some embodiments, the client device 185 is implemented by utilizing a mobile communication device such as a smartphone, wearable device, or other smart device worn or carried by the user during the fitness activity. The client processing device 430 executes operational instructions to cause the client device to process the sensor data to generate the motion data, fitness partner data, and/or display data. In an example embodiment of the present invention, a mobile communication device includes at least one processor such as client processing device 430, a memory such as client memory 410 that stores client application instructions, such as client application data 412, for execution by the at least one processor; a client display 420 such as a touchscreen display configured to display interactive interface 425 in conjunction with execution of the client application instructions, and further configured to receive user input to the interactive interface 425; and client interface 450, implemented by utilizing a short range wireless transceiver configured to communicate bidirectionally, via a short range wireless communication protocol, with a processing system integrated within eyewear worn by a user while performing a fitness activity, such as an on-board system of eyewear processing system 150 integrated within the eyewear 100.

The client application instructions, when executed by the at least one processor, cause the mobile communication device to receive, via the short range wireless transceiver, sensor data from at least one motion sensor integrated within the eyewear. A transit velocity vector is determined based on the sensor data, corresponding to a transit of the user during performance of the fitness activity. The transit velocity vector can indicate a transit pace and a transit direction. Head tracking data is determined based on the sensor data, corresponding to head movement of the user during performance of the fitness activity. The head tracking data can indicate a head orientation direction relative to the transit direction.

Fitness partner profile data is generated based on the user input to the interactive interface displayed by the touchscreen display device, for example, prior to the performance of the fitness activity. Appearance data corresponding to an appearance of the virtual fitness partner is generated. For example, the appearance data can be determined based on the fitness partner profile data. Perspective data is generated and can indicate a display size and display coordinates calculated based on a virtual position vector and the head orientation direction. The virtual position vector can be determined based on calculating relative velocity data based on the transit velocity vector and a partner velocity vector, and the virtual position vector can indicate a magnitude and a direction of a virtual position of the virtual fitness partner relative to a position of the user.

Event trigger monitoring data can be generated, for example, based on the sensor data. The event trigger monitoring data can indicate one of a plurality of fitness partner actions in response to determining that a corresponding one of a plurality of event trigger conditions has been met. Display data can be generated based on the perspective data, the event trigger monitoring data, and appearance data. The display data can be transmitted to the eyewear 100 via the short range wireless transceiver. The display data is displayed on at least one display device of eyewear to virtually superimpose the virtual fitness partner upon physical surroundings viewed by the user through at least one translucent lens of the eyewear to simulate performance of the fitness activity by the virtual fitness partner along a virtual transit within a physical vicinity of the user throughout the transit of the user. The virtual fitness partner is depicted to perform the one of the plurality of fitness partner actions in accordance with the event trigger monitoring data.

Figure 5:
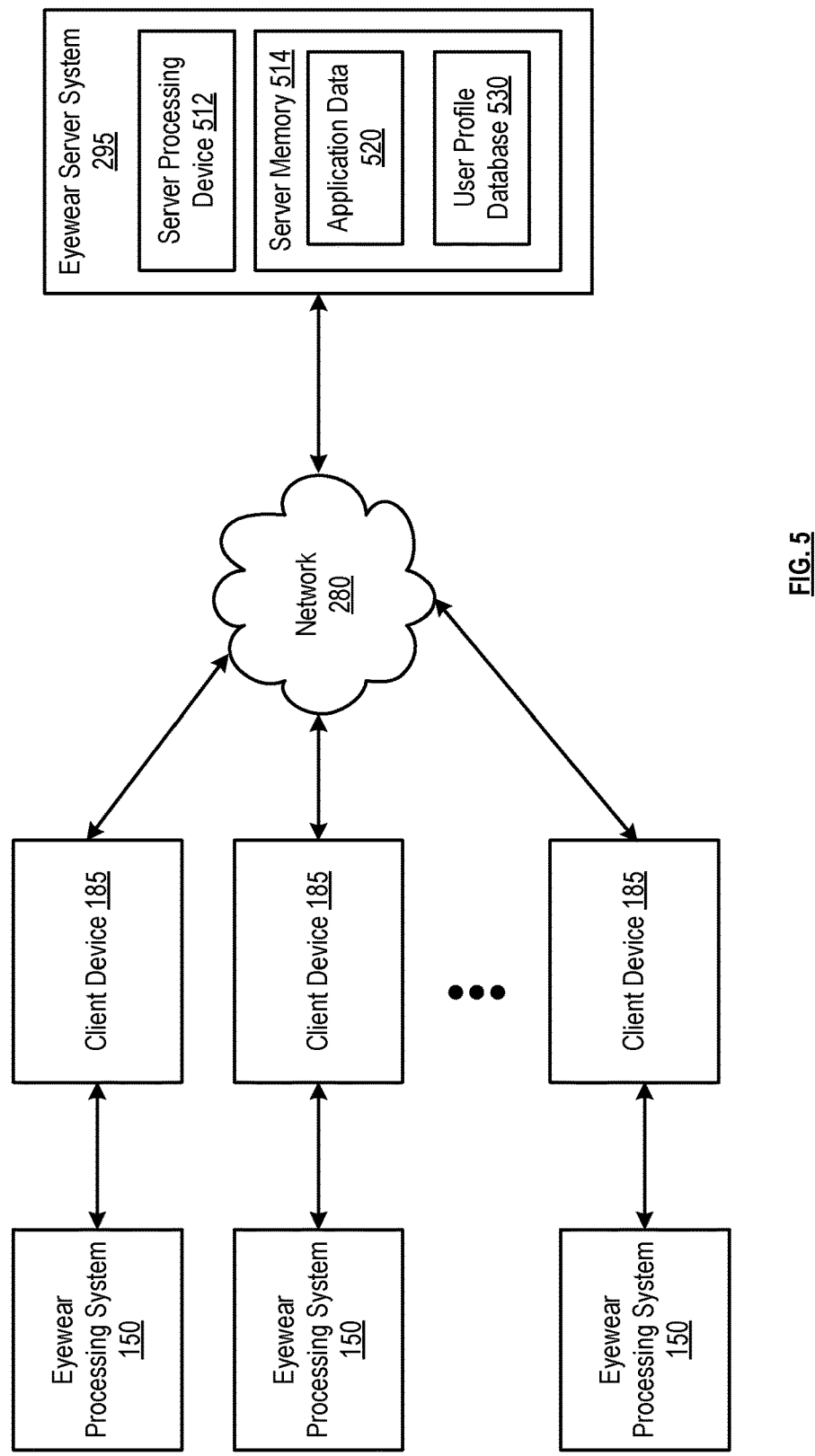
FIG. 5 is a schematic block diagram of an example embodiment of the present invention.

FIG. 5 presents a schematic block diagram of an embodiment of the present invention that includes a plurality of eyewear processing systems 150 and a corresponding plurality of client devices 185 of FIG. 3, corresponding to a plurality of users of the system. The plurality of client devices client 185 communicate bidirectionally with eyewear server system 295 of FIG. 2 via network 280. The eyewear server system 295 can include at least one server processing device 512 and/or at least one server memory 514. The server memory 514 can store application data 520, which can be transmitted to the plurality of client devices as some or all of client application data 412. The eyewear server system can also store a user profile database 530, which can include user profile data corresponding to the plurality of users of the system.

The user profile data of a user can include fitness activity history data that includes a plurality of workout entries corresponding to a plurality of workouts or other durations of performance of a fitness activity. Some or all entries of the fitness activity history data can include a plurality of motion logs 212 corresponding to data collected and/or generated by the eyewear processing system 150 for a plurality of durations that the user performed the same and/or different fitness activity along the same and/or different routes. For example, fitness activity history data of a user's user profile data can include data for several workouts corresponding to jogs, bike rides, and swim sessions. Some or all of the motion logs can be timestamped and/or location tagged. Some or all entries can include event log 214 to indicate indicates a plurality of events that were detected during some or all of the workouts, which can also be timestamped and/or location tagged events. Some or all entries can include fitness partner profile data 216 indicating characteristics such as appearance data, partner velocity data, or other configuration data relating to the virtual fitness partner depicted during the workout as discussed herein. The entries can also include logs corresponding to sensor data collected by other sensors, and can thus include, for example, an image log, a location log, a biometric data log, and/or an audio data log.

FIGS. 6A-6F illustrates sample displays on interactive interface 425, for example, in conjunction with execution of the client application data 412. Some or all of the data discussed with regards to FIGS. 6A-6F can be generated by the client device 185, the eyewear server system 295, and/or the eyewear processing system 150. For example, data generated by eyewear server system 295, and/or the eyewear processing system 150 can be sent to the client device 185 for display to the user via interactive interface 425. Some or all input data to interactive interface 425 can be processed by the client device directly and/or can be sent to eyewear server system 295, and/or the eyewear processing system 150.

Figure 6B:
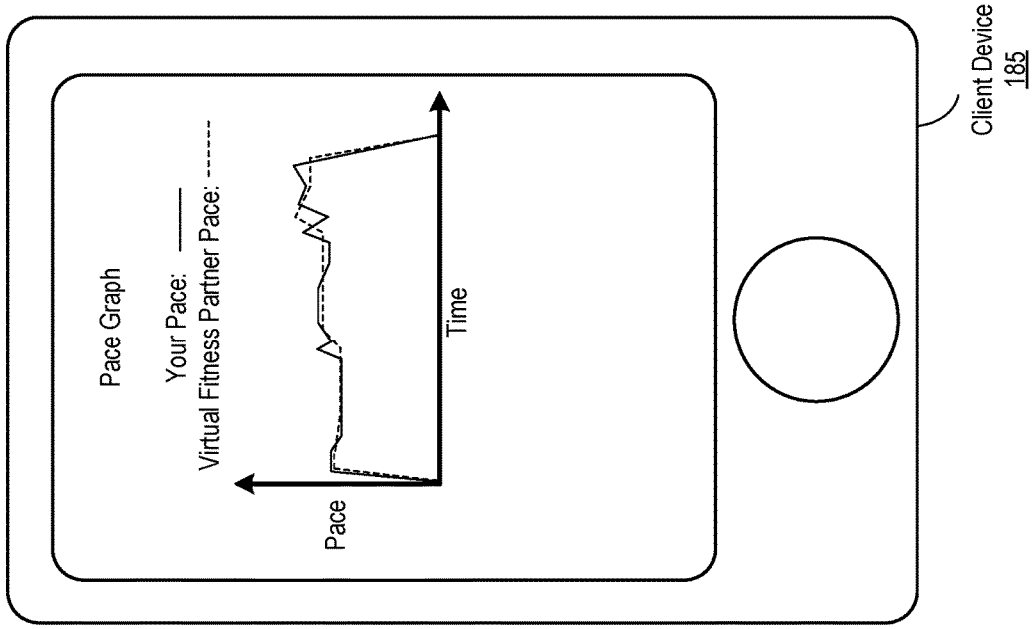
FIG. 6B is a graphical illustration of an example e user interface displayed on a client device in conjunction with various embodiments of the present invention.
Figure 6A:
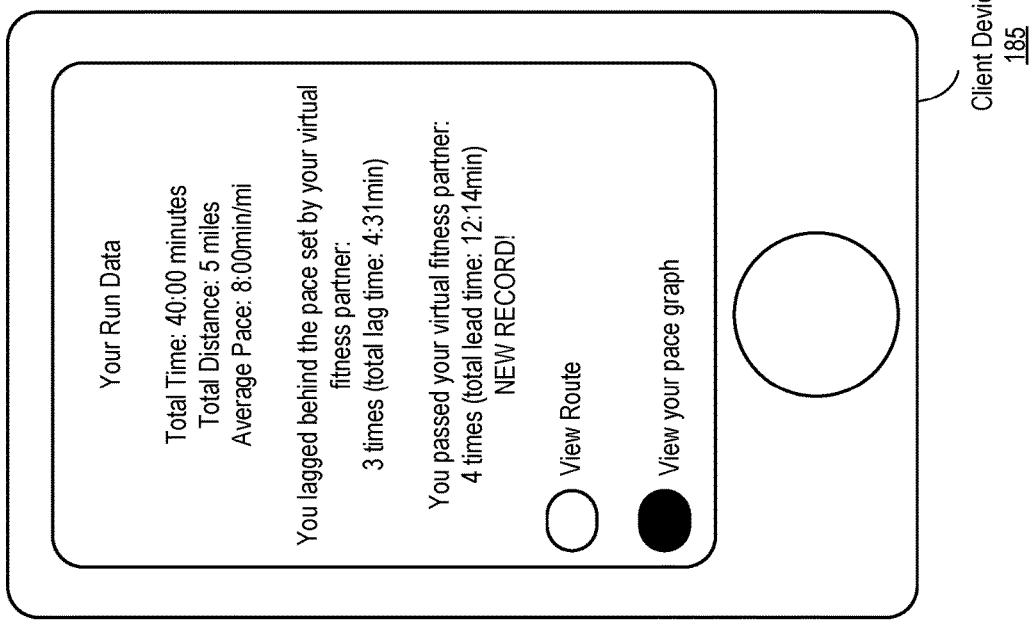
FIG. 6A is a graphical illustration of an example user interface displayed on a client device in conjunction with various embodiments of the present invention.

As shown in FIG. 6A, a user can view data corresponding to their most recent workout, and/or can view data corresponding to a selected one of the plurality of workout entries of their fitness activity history data of the user profile. Data of event log 214 can be displayed, for example, to indicate when, for how long, and/or how many times the user lagged behind the pace set by the virtual fitness partner, and/or how many times the user passed their virtual fitness partner. The user can elect to view the route of their run, for example, superimposed onto a map display as shown in FIG. 6B. The user can elect to view a pace graph of their run, for example, plotting their speed as a function of time based on the motion log 212. The user pace vs. time can be plotted in conjunction with the virtual fitness partner pace vs time for a visual depiction of when, for how long, and how many times the user passed or lagged behind their fitness partner's pace.

Figure 6D:
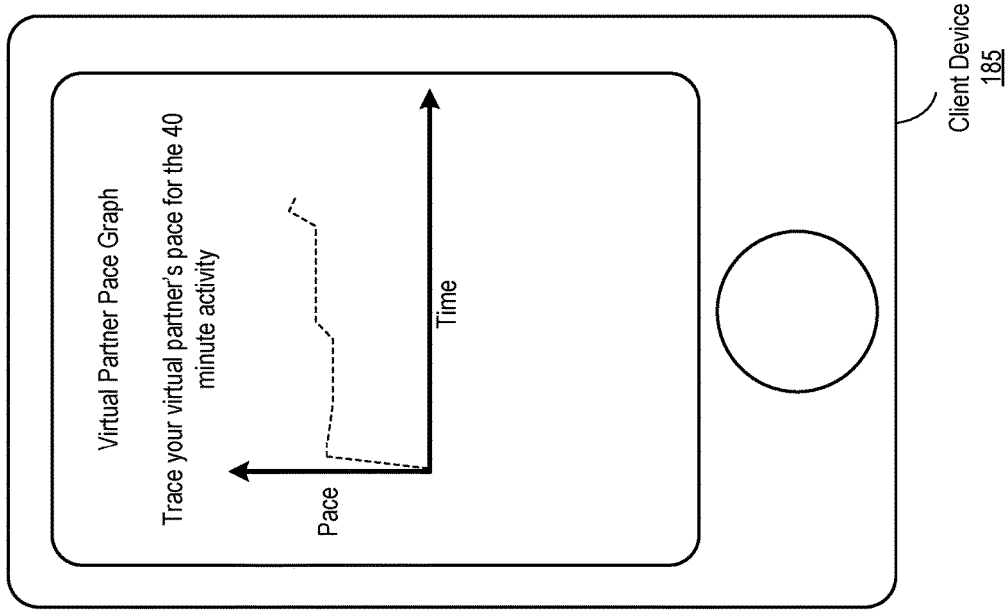
FIG. 6D is a graphical illustration of an example user interface displayed on a client device in conjunction with various embodiments of the present invention.
Figure 6C:
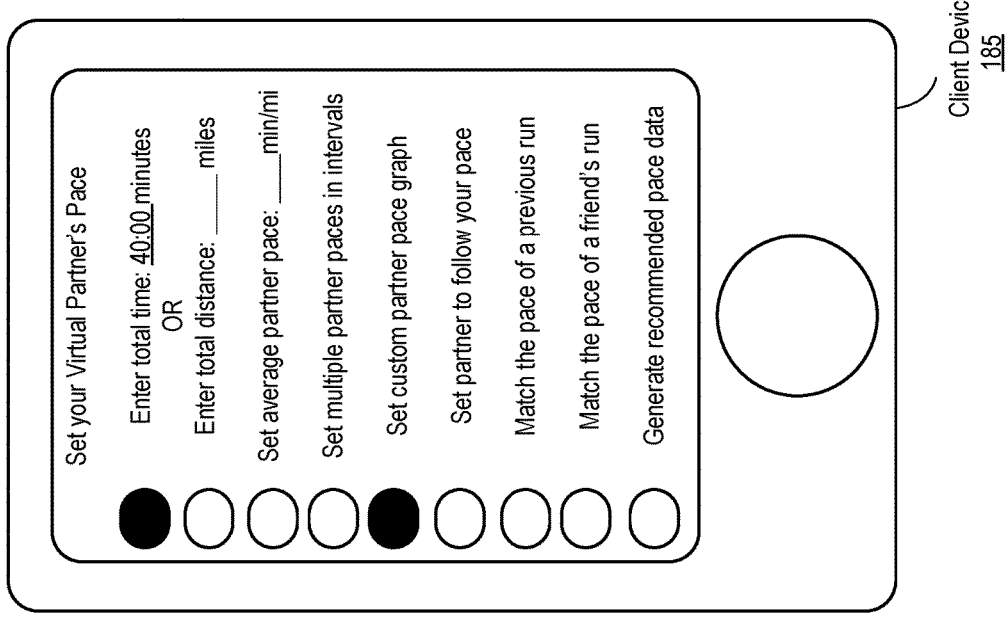
FIG. 6C is a graphical illustration of an example user interface displayed on a client device in conjunction with various embodiments of the present invention.

As shown in FIG. 6C, the user can customize their virtual fitness partner's pace. For example, user input to this interactive interface can be used to generate fitness partner profile data, and in particular, can be used to generate partner velocity vector data of the fitness partner profile data. In some embodiments, only the pace of one or more partner velocity vectors is configured in the interactive interfaces discussed, but the direction of the partner velocity vectors is determined in real-time to follow the direction of the user's transit, allowing the user to dynamically determine their transit route in real-time.

The user can enter a total time of their intended fitness activity. The fitness partner profile data will indicate that the virtual fitness partner will move in conjunction with their partner velocity vector data for a duration corresponding to the total time entered by the user. Alternatively or in addition, the user can enter a total distance of their fitness activity. The fitness partner profile data will indicate that the virtual fitness partner will move in conjunction with their partner velocity vector data for a distance corresponding to the total distance entered by the user. While the interactive interface for configuring virtual fitness partner pace data is shown, the user can similarly configure appearance data of their virtual fitness partner and/or event trigger conditions and/or the corresponding fitness partner actions.

The user can enter an average partner pace, for example, indicating that their virtual fitness partner should move at a constant speed corresponding to 6.5 minute miles. The virtual fitness partner will move in conjunction with a partner velocity vector of constant magnitude indicating a 6.5 minute mile pace, and/or the virtual fitness partner will move within a configured or predetermined pace differential window centered at a 6.5 minute mile pace. Alternatively, the user can set a plurality of partner paces in intervals, used to generate a plurality of partner velocity vectors that each correspond to an interval of time and/or a distance. For example, the user can select that their virtual fitness partner alternate between 7.5 minute miles and 6 minute miles every 5 minutes, and/or the user can select to run the first 5 miles at 6.5 minute miles and the second 5 miles at 7.5 minute miles. As another example, the user, with the knowledge that a long 0.5 mile hill begins at mile 4 of their route, can set their virtual fitness partner to run at a pace of 6.5 minute miles for the length of the route, with the exception of mile 4 to mile 4.5, where the virtual fitness partner instead is configured to run at a pace of 8.5 minute miles. In some embodiments, the interactive interface allows the user to set paces for their virtual fitness partner for different levels of elevation grade that may be encountered along the route, and the virtual fitness partner will automatically adjust its pace during the fitness activity accordingly in response to the eyewear processing system detecting corresponding changes in elevation grade along the route.

In some embodiments, the user can elect to set a custom pace graph, as shown in FIG. 6D, where a user used touch input and/or mouse input to trace and/or draw their virtual fitness partners pace as a function of time and/or distance for the desired time duration and/or distance duration of the fitness activity. This user generated pace graph can be used to generate a corresponding plurality of partner velocity vectors that can be timestamped and/or mapped to a corresponding time interval and/or distance interval in accordance with user generated pace graph.

In some embodiments, the interactive interface can display a map of a user's desired route, and can indicate a position on the map, along the route, that corresponds to a selected point of the virtual partner pace graph that corresponds to a position of the mouse and/or users finger along the pace graph. For example, the map can display that, based on the virtual fitness partner pace graph selected by the user, the virtual fitness partner will be crossing the intersection of main street and $1^{st}$ street 4 minutes and 32 seconds into the activity.

In some embodiments, the user can set their virtual fitness partner to match their pace and/or follow their pace, as discussed previously. In such embodiments, a subsequent interactive interface can allow the user to select the x-component and/or y-component of the virtual position vector, to select position differential window data for the virtual fitness partner, and/or path offset data that dictates the virtual position vector. In some embodiments, the user can simply indicate if they wish their virtual fitness partner to run ahead of them, beside them on their left, and/or beside them on their right, and the x-coordinate and/or y-coordinate will be generates automatically. In some embodiments, the user can enter this input while wearing eyewear 100. The user can enter user input to toggle a position of their virtual fitness partner displayed to the user in the display region while setting these preferences, enabling the user to visually determine a preferred virtual position vector.

In some embodiments, the user can set their virtual fitness partner to match a pace of a previous run. The fitness partner profile data such as partner velocity vector data can be based on prior transits indicated in the fitness activity history data, as discussed herein. For example, previous transits of the user can be replicated by the virtual fitness partner in future workouts, allowing the user to race and/or be paced by a virtual fitness partner that is following the pace and/or route of a prior transit by following the corresponding plurality of timestamped and/or location tagged partner velocity vectors of a prior transit of the user. For example, a personal best transit, a most recent transit, a transit corresponding to the current location of the user, or a particular transit selected by the user can be used to generate the fitness partner profile data to either match prior user results or to provide an improvement over prior results. In this fashion, fitness partner profile data can be generated to improve the total time by a certain value At or a certain time percentage, such as 1% of the total prior time of a personal best transit, a most recent transit or other prior results. A subsequent user interface can present motion log 212, event log 214, pace graphs, route data and/or other data corresponding to the plurality of workout entries, and the user can select one of the plurality of workout entries via input to the interactive interface. The pace graph, motion log 212, and/or event log

214 of the selected one of the plurality of workout entries will be used to generate a plurality of partner velocity vectors that each correspond to a timestamp, location, interval of time and/or a distance.

In some embodiments, the user can set their virtual fitness partner to match a pace of a friends run. For example, the user can select from a friend from a plurality of connections indicated in their user profile data, where the plurality of connections corresponds to a plurality of other user profiles of the eyewear server system. In the same fashion as viewing and selecting from workout entries of their own fitness activity history data, the user can view route data, pace graphs, motion log 212, event log 214, and/or other data corresponding to some or all of a plurality of workout entries of some or all of a plurality of connections. For example, the user can select a particular pace graph and/or route of a friend's prior transit, collected by an eyewear processing system 150 worn by the friend during the friend's prior transit, and stored in the friend's fitness activity history data by the eyewear server system 295. Such interactive interfaces are discussed in further detail in conjunction with FIGS. 6E and 6F.

In some embodiments, a user can configure which of their workout entries are made public to some or all of their connections, for example, allowing them to keep private an embarrassing workout entry logged on a day they were feeling under the weather or otherwise performed poorly. In some embodiments, users of the system can make some or all of their workout entries public to all users of the system, even if they are not connections. For example, workout entries corresponding to famous athletes can be made public to all users of the system, and/or to some users based on subscription payments to the system. As discussed herein, fitness partner profile data can also include appearance data corresponding to the friend, famous athlete, or other user of the system who fitness activity history data is used to generate the partner velocity vector data. This can be based on camera data collected to generate a two dimensional image and/or 360 degree image data of the other user of the system, stored in user profile data. This can also be based on the motion log 212, event log 214, or other data collected in conjunction with prior performances of the other user in the fitness activity history data of the other user. Thus, the virtual fitness partner can be depicted to look like the other user of the system; can be depicted to perform the fitness activity in the same form and/or style as the other user of the system; can be depicted to breathe, sweat, and/or visually exhibit varying levels of physical fatigue at the same time during the route and/or the same manner as the other user of the system; and/or can depicted to say phrases, make gestures, and/or share other mannerisms with the other user of the system at the same time during the route and/or in the same manner as the other user of the system.

The user can select that their virtual fitness partner's pace be set in accordance with recommended pace data generated by the system. In some embodiments, the client device can automatically generate partner velocity vector data intelligently, based on trends and/or patterns indicated in entries of the fitness activity history data and/or based on current conditions for the present fitness activity the user is planning to undergo. This can also be based on trends and patterns determined across the plurality of users of the eyewear server system.

In some embodiments, the plurality of workout entries can be processed to generate aggregate statistics for the user such as average pace, average pace as a function of elevation grade, average pace as a function of environmental conditions detected by the sensors and included in the workout entry, average pace as a function of location, average pace as a function of time of day or time of week, average pace as a function of biometric data such as weight, nutrition data for meals eaten, and/or hours or sleep, and/or other aggregate statistics. Other information can be determined as a function of some or all of these factors, such as workout duration, acceleration data, average heartrate, number of stops during the workout, breathing rate, rating of user form while performing the activity, or other data collected in the entries and analyzed by the system. This information can be determined based on user input to the interactive interface to populate this data in corresponding workout entries, and/or can be determined automatically by the eyewear processing system based on sensor data. Some or all of this data can be displayed to the user via the interactive interface to aid the user in determining how these factors contribute to workout performance and/or allow the user to set goals and track their progress over time.

This data can be used by the eyewear processing system 150 to automatically determine custom fitness partner profile data for a current workout. For example, in response to determining that a user tends to run 6.5 minute miles on Sunday mornings on 8 hours of sleep the virtual fitness partner can be configured to run at a pace in accordance with a 6.5 minute mile in response to the eyewear processing system 150 determining that a current run performed by the user is on Sunday morning and/or that the user has slept 8 hours. In response to determining that the user tends to run at a slower pace of 7 minute miles on Thursday evenings with 5 hours of sleep, the virtual fitness partner can be configured to run at a pace in accordance with a 7 minute mile in response to the eyewear server system 295, client device 185, and/or eyewear processing system 150 determining that a current run performed by the user is on Thursday evening and/or that the user has slept 5 hours. Contrarily, the eyewear processing system 150 could instead determine to push the user in these unideal conditions by maintaining a virtual fitness partner pace of 6.5 minute miles, and including appearance data and/or event triggering data for a more motivational fitness partner.

Some of the aggregate statistics can be based on features of the virtual fitness partner in the fitness partner profile data corresponding to workout entries. For example, the aggregate statistics can include average pace as a function of virtual fitness partner appearance data and/or average pace and/or acceleration as a function of virtual fitness partner pace and/or acceleration. Average pace, acceleration, and/or other factors can be determined as a function of some or all of the plurality of fitness partner actions. For example, the eyewear processing system can determine that the user picks up their pace more frequently in response to motivational thumbs up by their virtual fitness partner, and that the user tends to pick up their pace less frequently when the user gives derogatory feedback. As another example, the eyewear processing system can determine that the user has a faster pace and/or performs the activity for longer durations when their virtual fitness partner is following a predetermined plurality of partner velocity vectors, and/or that user has a slower pace and/or works out for shorter durations when their virtual fitness partner is instead abiding by a predetermined virtual position vector. As another example, the eyewear processing system can determine that the user matches acceleration changes in response to their virtual fitness partner alternating between sprints and slow jogs every 3 minutes, but that the user fails to match acceleration changes when their virtual fitness partner alternates between sprints and slow jogs every 1 minute. As another example, the eyewear processing system can determine that the user matches faster paces set by their virtual fitness partner more consistently when their virtual fitness partner depicts an attractive fitness partner, and tends to lag behind more frequently when their virtual fitness partner depicts an old fitness partner. As another example, the eyewear processing system can determine that the user passes their virtual fitness partner more consistently when their virtual fitness partner depicts a coworker with whom they are competitive than when their virtual fitness partner depicts non-competitive friends of the user. This information can similarly be used to customize the fitness partner profile data for a current workout to best enhance the user's performance and/or experience, and/or can be displayed via the interactive interface to aid the user in configuring the fitness partner profile data for future workouts.

Figure 6F:
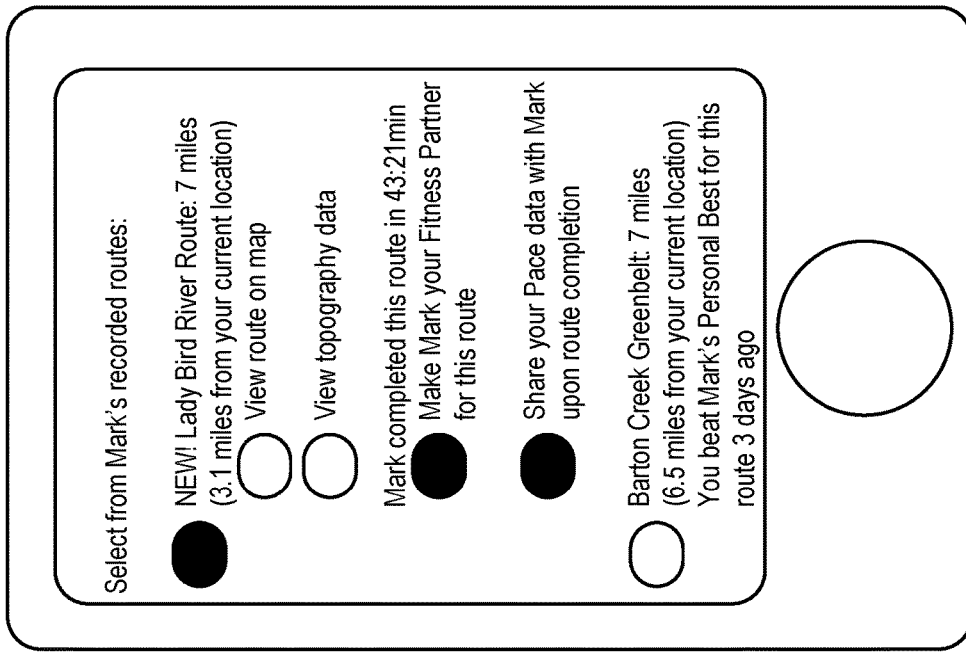
FIG. 6F is a graphical illustration of an example user interface displayed on a client device in conjunction with various embodiments of the present invention.
Figure 6E:
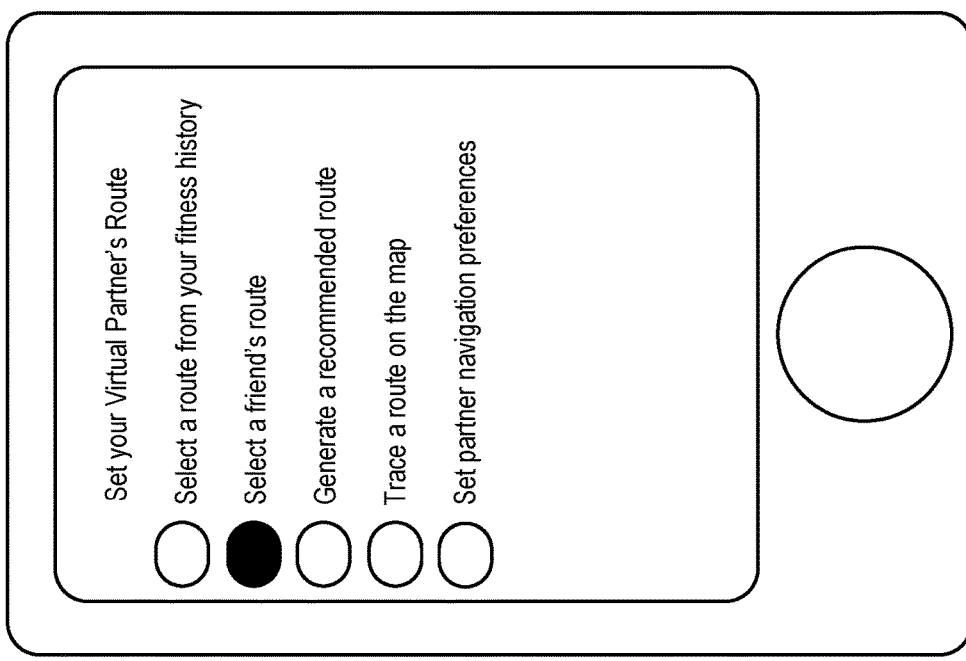
FIG. 6E is a graphical illustration of an example user interface displayed on a client device in conjunction with various embodiments of the present invention.

FIG. 6E illustrates an example interactive interfaces corresponding to selecting the route followed by their virtual fitness partner. This can be used in embodiments where the partner velocity vector data includes location tagged unit vectors indicating direction only, and/or where the partner velocity vector data otherwise indicates navigation data but still adapts to the pace of the user in conjunction with a configured virtual position vector. This can also be used in embodiments where both pace and direction of a time-stamped and/or location tagged plurality of partner velocity vectors of a prior transit are utilized.

The user can select a route from their fitness activity history data and/or from a friend's fitness activity history data for example, selecting a route corresponding to one of a plurality of the user's workout entries and/or selecting a route corresponding to one of a plurality of workout entries corresponding to friends of the user or other users in of the system. As shown in FIG. 6F, the user can be presented with a plurality of routes, and can view the time taken to complete the route in corresponding transit of the workout entry, the distance of the route, elevation and/or topography data such as an elevation graph plotting elevation vs distance, map data presenting the route on a map, navigation data presenting navigation instructions, a distance of the start of the route from the current location of the user determined by the client device, names and/or pictures of landmarks or other sights along the route, and/or other data associated with the route. The plurality of routes displayed to the user can include prior transits of the user and/or prior transits of other users of the system, as shown in FIG. 6F.

In some embodiments, a recommended route can be generated for the user based on aggregate statistics generated for prior transits as previously discussed, in a similar fashion as the pace data. Additionally, the average distance of the user's transits can be used to select a route of a similar distance, and/or average elevation change of the user's transit can be used to select a route with similar elevation change. If prior transits by the user indicate that the user tends to prefer transits along pathways in parks as opposed to street-side sidewalks, a scenic park route can be selected for the user accordingly. If prior transits indicate that the user likes to end their transit at a type of establishment, such as a coffee shop, a route ending at the same type of establishment can be selected for the user accordingly. Known routes logged by the user and/or by other users of the system can be used to generate possible routes selected for the user. In some embodiments, a plurality of options can be generated for recommendation to the user, and the user can select from the plurality options.

A distance from the user's current location to a plurality of known routes can be used to select a route closest or within a configured range of the current location of the user determined by the current location of the client device and/or eyewear processing system, and/or can be used to select a starting point along the route that is closest to or within the preconfigured range of the user. A route from the user to the start of the known route can be generated based on navigation data and appended to the start of the route and/or a route from the end of the known route to the user's starting location or a configured ending location can be appended to the end of the route. These appended start and/or end routes can be used to generate additional partner velocity vector data, such that the virtual fitness partner leads the user to the start and from the end of the known route.

In some embodiments, the user can trace a route on a map and/or can otherwise select the route by interacting with a map displayed on the interactive interface via user input. In such embodiments the map can display the user's current location as determined by the client system based on location data, and the user can trace a route that starts from their current location. In some embodiments, a user can trace a route, and navigation data can automatically be generated from the user's current location to the start of the route. In some embodiments, this additional navigation data can be used to append an additional portion of the transit route from the user's starting location. The route generated by user input to the map can be used to generate the partner velocity vector data, such that the virtual fitness partner follows the route selected on the map.

In some embodiments, partner navigation preferences can be set in a subsequent interactive interface. For example, the user can elect that their virtual fitness partner leads the way to navigate along the predetermined route. The user can elect that their virtual fitness partner be visually depicted to point towards a new direction in conjunction with navigation data of the route indicating it is time to turn. In some embodiments the user can elect that their virtual fitness partner be depicted to vocalize the navigation instructions, such that the navigation instructions are presented as audio data for delivery to the user via speaker 270. In some embodiments the user can elect that navigation data be superimposed visually upon the display by the display device, such that an arrow, highlighting, or other indication of navigation instructions and/or the route to follow be superimposed upon the physical path corresponding to the route.

FIG. 6F illustrates options that can be presented to the user in embodiments where the user selects a friend's route. In some embodiments, the user can also elect to select the pace data corresponding to the transit of the friend along the selected route to generate pace data for the partner velocity vector data, and/or the corresponding pace data will automatically be utilized to generate the partner velocity vector data. In this fashion the virtual fitness partner can be set to follow the route at the same set of paces as performed by the friend, collected as motion data and/or location data as the friend completed the corresponding prior transit and indicated in the workout entry. This can be utilized to allow the user to virtually exercise with their friend along the route, as their virtual fitness partner is configured to move along the same path at the same pace as their friend previously did. Event log data, other motion data, and/or microphone data collected in the prior transit can also be utilized to configure display data and/or audio data corresponding to the virtual fitness partner to further simulate the performance of the fitness activity by the friend. For example, the breathing patterns of the friend, form and stride length of the friend, arm motions of the friend, and/or recorded statements made by the friend such as "this hill is tough!" can be collected by the eyewear processing system associated with the friend as timestamped and/or location tagged data during the friends transit, and the virtual fitness partner can be simulated to perform the fitness activity with the same form, breathing patterns, actions, and/or statements at the same time and/or same location along the transit.

In some embodiments, a group of users that all have workout entries corresponding to the same route can allow the users to virtually workout as a group in future transits along the same route. For example, a user can select multiple virtual fitness partners to be displayed and to virtually perform the fitness activity along the route with them, in accordance with corresponding workout entries of multiple friends of the user taken along the route.

In some embodiments the eyewear server system can track race data between two or more users in the system for one or more routes. For example, a personal best, or most recent performance along the route, can be used to generate corresponding virtual fitness partner displayed to other users of the system. As a user completes their fitness activity, a winner can be determined, where the winner is the user or one of the plurality of virtual fitness partners displayed to the user. For example, the winner can correspond to determining which of the user or the plurality of virtual fitness partners completes the route first. The user corresponding to a virtual fitness partner that won the race can be notified that they are the winner and/or the user corresponding to a virtual fitness partner that lost the race can be notified that they lost the race, or can otherwise be notified of their placement in the race, via display on the interactive interface of their client device. The eyewear server system can track the best time for each of the plurality of routes by each user in a group of friends, and/or between the user and a single rival to determine the longstanding winner of each route. In some embodiments virtual fitness partners corresponding to a first user will automatically be generated to follow the pace of the most current transit of the first user along the route. A second user that is virtual racing the first user will thus be displayed a virtual fitness partner that corresponds to the most current transit of the first user. The eyewear server system can subsequently determine that the workout entry of the second user in their virtual race against the first user be used to generate a virtual fitness partner for display to the first user, allowing the first user to virtually race the second user based upon the most recent transit of the second user. This process can continue alternating back and forth, where the winner of each race is tracked, for example, encouraging users to always put in their best effort for each race.

Figure 7:
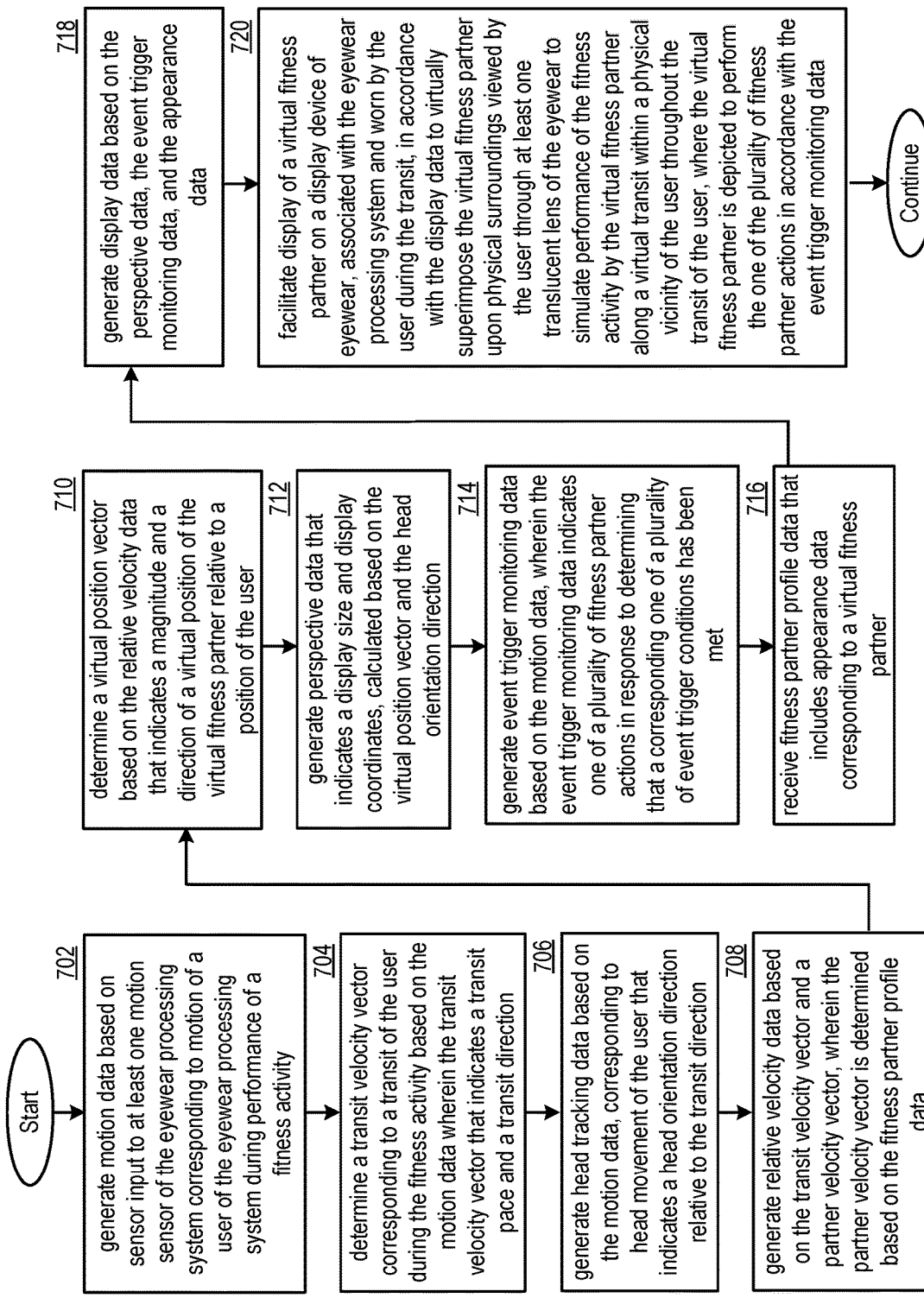
FIG. 7 is a flowchart representation of a method in accordance with an embodiment of the present invention.

FIG. 7 is a flowchart illustrating an example of a method for use in association with one or more functions and features described in conjunction with FIGS. 1-6F, for execution by an eyewear processing system 150 that includes at least one processing device and memory that stores instruction that configure the at least one processor to perform the steps described herein. Some or all of the steps can be performed by a processing system of eyewear, an off-board device that includes at least one processing device and memory and/or a client device that includes at least one processing device and memory, where the eyewear processing system 150 is communicating with the off-board device and/or client device, and/or where some or all of the eyewear processing system 150 is integrated within eyewear, an off-board device, and/or a client device.

Step 702 includes generating motion data based on sensor input to at least one motion sensor of the eyewear processing system corresponding to motion of a user of the eyewear processing system during performance of a fitness activity. Step 704 includes determining a transit velocity vector corresponding to a transit of the user during the fitness activity based on the motion data wherein the transit velocity vector that indicates a transit pace and a transit direction. Step 706 includes generating head tracking data based on the motion data, corresponding to head movement of the user that indicates a head orientation direction relative to the transit direction. Step 708 includes generating relative velocity data based on the transit velocity vector and a partner velocity vector. Step 710 includes determining a virtual position vector based on the relative velocity data that indicates a magnitude and a direction of a virtual position of a virtual fitness partner relative to a position of the user.

Step 712 includes generating perspective data that indicates a display size and display coordinates, calculated based on the virtual position vector and the head orientation direction. Step 714 includes generating event trigger monitoring data based on the motion data, where the event trigger monitoring data indicates one of a plurality of fitness partner actions in response to determining that a corresponding one of a plurality of event trigger conditions has been met. Step 716 includes receiving fitness partner profile data that includes appearance data corresponding to a virtual fitness partner. For example, the fitness partner profile data can be generated based on user input to an interactive interface of a client device associated with the user, and can be received from the client device via a network. In some embodiments, the partner velocity vector is determined based on the fitness partner profile data.

Step 718 includes generating display data based on the perspective data, the event trigger monitoring data, and the appearance data. Step 720 includes facilitating display of the virtual fitness partner on a display device of eyewear, associated with the eyewear processing system and worn by the user during the transit, in accordance with the display data to virtually superimpose the virtual fitness partner upon physical surroundings viewed by the user through at least one translucent lens of eyewear to simulate performance of the fitness activity by the virtual fitness partner along a virtual transit within a physical vicinity of the user throughout the transit of the user, where the virtual fitness partner is depicted to perform the one of the plurality of fitness partner actions in accordance with the event trigger monitoring data. For example, the display device is a heads-up display that projects the virtual fitness partner onto the at least one translucent lens of the eyewear. In various embodiments, the display data corresponds to stereoscopic data.

Figure 8:
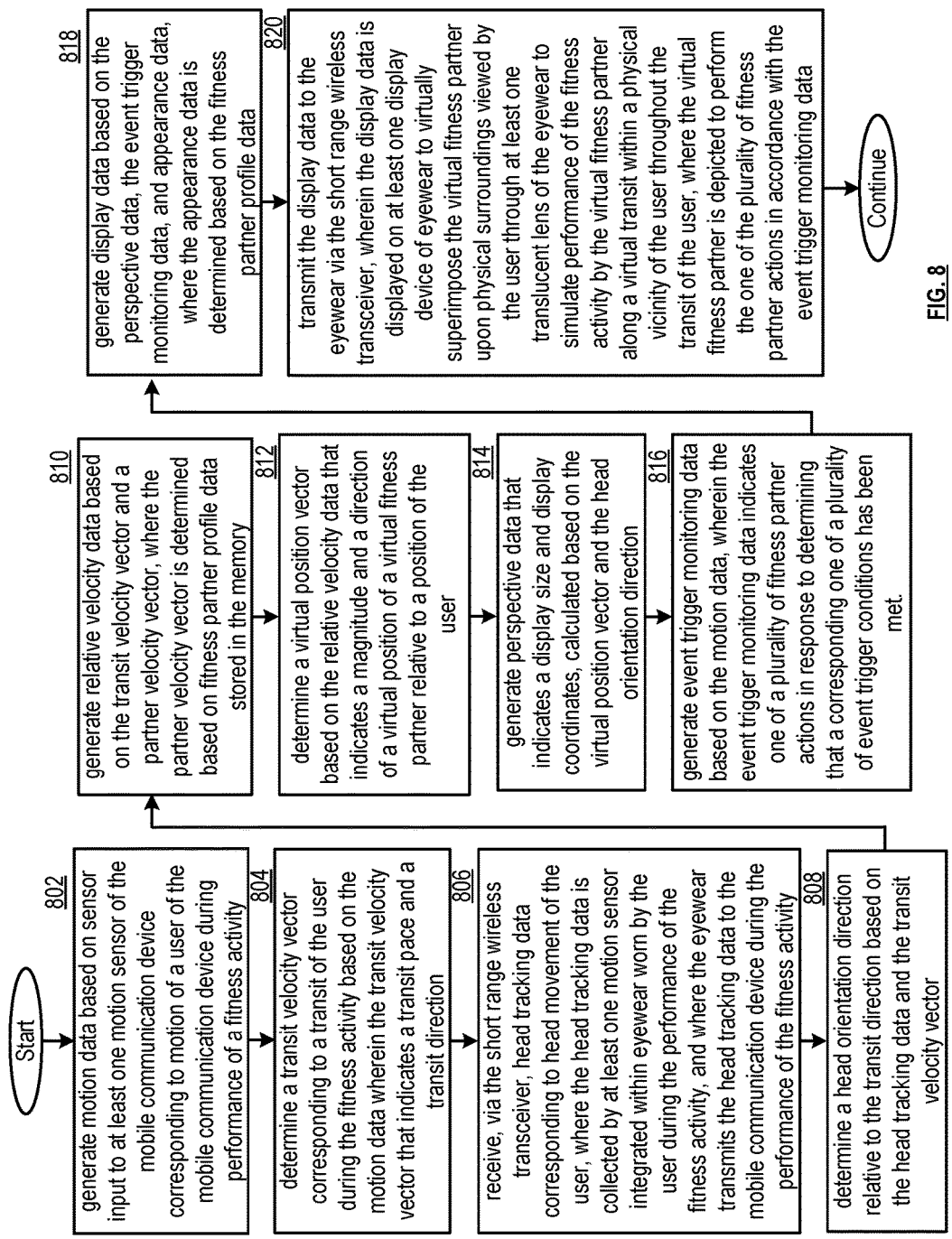
FIG. 8 is a flowchart representation of a method for execution by a mobile communication device in accordance with an embodiment of the present invention.

FIG. 8 is a flowchart illustrating an example of a method for use in association with one or more functions and features described in conjunction with FIGS. 1-7, for execution by a mobile communication device, such as client device 185, off-board device 253, and/or another device that includes a memory, at least one processor, and a short range wireless transceiver. The method is executed in conjunction with mobile application instructions stored by the memory device that, when executed by the at least one processor, cause the mobile communication device to perform the steps described herein.

Step 802 includes generating motion data based on sensor input to at least one motion sensor of the mobile communication device corresponding to motion of a user of the mobile communication device during performance of a fitness activity. Step 804 includes determining a transit velocity vector corresponding to a transit of the user during the fitness activity based on the motion data wherein the transit velocity vector that indicates a transit pace and a transit direction. Step 806 includes receiving, via the short range wireless transceiver, head tracking data corresponding to head movement of the user. The head tracking data is collected by at least one motion sensor integrated within eyewear worn by the user during the performance of the fitness activity, and the eyewear transmits the head tracking data to the mobile communication device during the performance of the fitness activity.

Step 808 includes determining a head orientation direction relative to the transit direction based on the head tracking data and the transit velocity vector. Step 810 includes generating relative velocity data based on the transit velocity vector and a partner velocity vector, where the partner velocity vector is determined based on fitness partner profile data stored in the memory. Step 812 includes determining a virtual position vector based on the relative velocity data that indicates a magnitude and a direction of a virtual position of a virtual fitness partner relative to a position of the user. Step 814 includes generating perspective data that indicates a display size and display coordinates, calculated based on the virtual position vector and the head orientation direction. Step 816 includes generating event trigger monitoring data based on the motion data, wherein the event trigger monitoring data indicates one of a plurality of fitness partner actions in response to determining that a corresponding one of a plurality of event trigger conditions has been met.

Step 818 includes generating display data based on the perspective data, the event trigger monitoring data, and appearance data, where the appearance data is determined based on the fitness partner profile data. Step 820 includes transmitting the display data to the eyewear via the short range wireless transceiver, wherein the display data is displayed on at least one display device of eyewear to virtually superimpose the virtual fitness partner upon physical surroundings viewed by the user through at least one translucent lens of the eyewear to simulate performance of the fitness activity by the virtual fitness partner along a virtual transit within a physical vicinity of the user throughout the transit of the user, where the virtual fitness partner is depicted to perform the one of the plurality of fitness partner actions in accordance with the event trigger monitoring data.

In various embodiments, one of the plurality of event trigger conditions can include determining that an angle between a head orientation direction and the direction of the virtual position vector compares favorably to a threshold. In some embodiments, one of the plurality of event trigger conditions includes determining that the transit pace is below a slow pace threshold. Similarly, one of the plurality of event trigger conditions can include determining that the transit pace is below a fast pace threshold. The fast pace threshold and/or the slow pace threshold can be predetermined, can be configured by the user, and/or can be indicated in the fitness partner profile data.

In various embodiments, one of the plurality of event trigger conditions includes determining that a magnitude of a scalar projection of the virtual position vector onto a vector corresponding to the transit direction exceeds a lag threshold. The lag threshold can be predetermined, can be configured by the user, and/or can be indicated in the fitness partner profile data. The corresponding one of the plurality of fitness partner actions can include changing a magnitude of the partner velocity vector from a first pace to a second pace that is slower than the first pace. In various embodiments, a second one of the plurality of event trigger conditions includes determining that the magnitude of the scalar projection of the virtual position vector onto the vector corresponding to the transit direction no longer exceeds the lag threshold, and the corresponding one of the plurality of fitness partner actions includes resetting the magnitude of the partner velocity vector to the first pace.

In various embodiments, one of the plurality of event trigger conditions includes determining that a magnitude of a scalar projection of the virtual position vector onto a vector that is orthogonal to the transit direction exceeds a gap threshold. The gap threshold can be predetermined, can be configured by the user, and/or can be indicated in the fitness partner profile data. The corresponding one of the plurality of fitness partner actions includes setting a first updated direction to generate a first updated partner velocity vector, wherein the magnitude of a first cross product of the first updated partner velocity vector and the transit velocity vector is nonzero. A second one of the plurality of event trigger conditions can include determining that the magnitude of the scalar projection of the virtual position vector onto the vector that is orthogonal to the transit direction no longer exceeds the gap threshold. A second one of the plurality of fitness partner actions corresponding to the second one of the plurality of event trigger conditions can include setting a second updated direction to generate a second updated partner velocity vector, where the magnitude of a second cross product of the second updated partner velocity vector and the transit velocity vector is less than the magnitude of the first cross product.

In some embodiments, one of the plurality of event trigger conditions includes detecting a change in transit direction from a first direction to a second direction, and the corresponding one of the plurality of fitness partner actions includes setting an updated direction of the partner velocity vector in accordance with the change in transit direction. In some embodiments, the one of the plurality of event trigger conditions includes determining that a direction of vector projection of the virtual position vector onto a vector corresponding to the transit direction is opposite the transit direction. In some embodiments, the one of the plurality of event trigger conditions includes determining that a derivative of the transit pace exceeds a transit pace derivative threshold. The transit pace derivative threshold can be predetermined, can be configured by the user, and/or can be indicated in the fitness partner profile data.

In some embodiments, one of the plurality of fitness partner actions includes a positive encouragement gesture. In some embodiments, at least one speaker associated with the eyewear processing system plays auditory feedback to the user in conjunction with the one of the plurality of fitness partner actions, where the auditory feedback corresponds to vocal feedback by the virtual fitness partner.

The appearance data can indicate an avatar to be depicted in the display of the virtual fitness partner. In some embodiments, one of the plurality of fitness partner actions includes changing the virtual fitness partner from depicting a first avatar to depicting a second avatar. The first avatar and/or the second avatar can be indicated in the appearance data of the fitness partner profile data. In some embodiments, a plurality of different fitness partners is displayed to the user during the transit, and a plurality of corresponding avatars can be indicated in the appearance data of the fitness partner profile data. In some embodiments, one of the plurality of event trigger conditions includes determining a subset of the plurality of virtual fitness partners to be displayed to the user.

In various embodiments, the event trigger monitoring data is further based on voice input by the user to a microphone associated with the eyewear processing system. One of the plurality of fitness partner actions can correspond to one of a plurality of vocal commands by the user. Similarly, the motion data can include gesture data, and the event trigger monitoring data is further based on gesture input by the user. One of the plurality of fitness partner actions can correspond to one of a plurality of gesture commands by the user.

In various embodiments, the received fitness partner profile data can include a plurality of partner velocity vectors and a corresponding plurality of interval times. The virtual transit of the virtual fitness partner is displayed in accordance with the plurality of partner velocity vectors and a corresponding plurality of interval times. In various embodiments, the plurality of partner velocity vectors and the corresponding plurality of interval times are generated by the client application based on a plurality of previous transit velocity vectors and a corresponding plurality of previous timestamps generated by the motion data generator in a previous duration of the fitness activity by the user or by a different user. For example, the plurality of partner velocity vectors and the corresponding plurality of interval times can replicate the plurality of previous transit velocity vectors and time-lapses between the corresponding plurality of previous timestamps. As another example, the plurality of partner velocity vectors and the corresponding plurality of interval times improve upon the previous performance of the fitness activity, for example, by increasing some or all of the plurality of previous transit velocity vectors and/or by shortening some or all of the time-lapse between the corresponding plurality of previous timestamps.

In various embodiments, a communication interface associated with the eyewear processing system transmits a plurality of transit velocity vectors of the motion data and a corresponding plurality of timestamps corresponding to a duration of the fitness activity. A client application accesses the plurality of transit velocity vectors of the motion data and the corresponding plurality of timestamps to generate aggregate fitness activity data for display by a client device associated with the eyewear processing system via an interactive interface. The client application can update fitness activity history data in response to generating the aggregate fitness activity data, where the fitness activity history data includes a plurality of aggregate fitness activity data corresponding to a plurality of performances of the fitness activity performed by the user. In various embodiments, the plurality of partner velocity vectors of the fitness partner profile data is generated based on selecting one of the plurality of performances of the fitness activity in the fitness activity history data that corresponds to a personal best. As another example, the plurality of partner velocity vectors the fitness partner profile data is generated based on generating an average of some or all of the plurality of performances of the fitness activity in the fitness activity history data.

In various embodiments, the fitness activity history data includes route data corresponding to some or all of the plurality of performances of the fitness activity. Generating the fitness partner profile data includes determining a current route of the fitness activity, and generating the fitness partner profile data further includes identifying one of the plurality of performances of the fitness activity in the fitness activity history with a corresponding route data that compares favorably to the current route. The communication interface can transmit a plurality of locations collected by a geolocation sensor associated with the eyewear processing system, where each of the plurality of locations corresponding to the plurality of transit velocity vectors and/or the plurality of timestamps. Identifying one of the plurality of performances of the fitness activity with corresponding route data that compares favorably to the current route can include determining that a current location collected by the geolocation sensor compares favorably to location data indicated in the route data of the fitness activity history data.

In various embodiments, the client device communicates bidirectionally with a server via a wireless network. The server can store a plurality of user profiles corresponding to a plurality of users. The plurality of transit velocity vectors and the corresponding plurality of timestamps can be transmitted from the client device to the server via a wireless network. The server can update a first one of the plurality of user profiles corresponding to the user in response to receiving the plurality of transit velocity vectors and the corresponding plurality of timestamps. The server can transmit profile data stored in a second one of the plurality of user profiles to the client device. This profile data can include a second plurality of transit velocity vectors and a second corresponding plurality of timestamps. The plurality of partner velocity vectors and the corresponding plurality of interval times can be generated based on the second plurality of transit velocity vectors and the second corresponding plurality of timestamps, for example, to cause the virtual fitness partner to replicate a previous performance of the fitness activity by a second user associated with the second one of the plurality of user profiles.

The profile data can further include second user appearance data, and the virtual fitness partner can be displayed to resemble the second user, based on the second user appearance data. For example, the second one of the plurality of user profiles can correspond to a famous athlete, and the plurality of partner velocity vectors and the corresponding plurality of interval times can correspond to a previous performance of the fitness activity by of the famous athlete. As another example, the second one of the plurality of user profiles can corresponds to a friend of the user. For example, the first one of the plurality of user profiles can indicate a plurality of friends that includes the friend. The plurality of partner velocity vectors and the corresponding plurality of interval times correspond to a performance of the fitness activity by the friend.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. Eyewear worn by a user while performing a fitness activity, comprising:
    at least one sensor configured to register motions made by the user;
    at least one translucent lens, wherein a surface of the at least one translucent lens includes a display region;
    a motion data generator that processes input data collected by the at least one sensor to generate motion data, wherein the motion data includes:
        a transit velocity vector corresponding to a transit of the user during the fitness activity that indicates a transit pace and a transit direction; and
        head tracking data corresponding to head movement of the user that indicates a head orientation direction relative to the transit direction;
    a communication interface that receives fitness partner profile data, wherein the fitness partner profile data is configured by the user by utilizing a client application associated with the eyewear via input to an interactive interface displayed by a client device associated with the user;
    a fitness partner generator that generates display data associated with a virtual fitness partner, wherein the display data is based on:
        appearance data corresponding to an appearance of the virtual fitness partner, wherein the appearance data is determined based on the fitness partner profile data;
        perspective data that indicates a display size and display coordinates calculated based on a virtual position vector and the head orientation direction, wherein the virtual position vector is determined based on calculating relative velocity data based on the transit velocity vector and a partner velocity vector, and wherein the virtual position vector indicates a magnitude and a direction of a virtual position of the virtual fitness partner relative to a position of the user; and
        event trigger monitoring data based on the motion data, wherein the event trigger monitoring data indicates one of a plurality of fitness partner actions in response to the fitness partner generator determining that a corresponding one of a plurality of event trigger conditions has been met; and
    a display device that displays the virtual fitness partner within the display region in accordance with the display data to virtually superimpose the virtual fitness partner upon physical surroundings viewed by the user through the at least one translucent lens to simulate performance of the fitness activity by the virtual fitness partner along a virtual transit within a physical vicinity of the user throughout the transit of the user, and wherein the virtual fitness partner is depicted to perform the one of the plurality of fitness partner actions in accordance with the event trigger monitoring data.

2. The eyewear of claim 1, wherein the one of the plurality of event trigger conditions includes determining that an angle between a head orientation direction and the direction of the virtual position vector compares favorably to a threshold.

3. The eyewear of claim 1, wherein the one of the plurality of event trigger conditions includes determining that a magnitude of a scalar projection of the virtual position vector onto a vector corresponding to the transit direction exceeds a lag threshold, and wherein the lag threshold is indicated in the fitness partner profile data.

4. The eyewear of claim 3, wherein the corresponding one of the plurality of fitness partner actions includes changing a magnitude of the partner velocity vector from a first pace to a second pace that is slower than the first pace.

5. The eyewear of claim 1, wherein the one of the plurality of event trigger conditions includes determining that a magnitude of a scalar projection of the virtual position vector onto a vector that is orthogonal to the transit direction exceeds a gap threshold, and wherein the corresponding one of the plurality of fitness partner actions includes setting a first updated direction to generate a first updated partner velocity vector, wherein the magnitude of a first cross product of the first updated partner velocity vector and the transit velocity vector is nonzero.

6. The eyewear of claim 5, wherein a second one of the plurality of event trigger conditions includes determining that the magnitude of the scalar projection of the virtual position vector onto the vector that is orthogonal to the transit direction no longer exceeds the gap threshold, and wherein a second one of the plurality of fitness partner actions corresponding to the second one of the plurality of event trigger conditions includes setting a second updated direction to generate a second updated partner velocity vector, wherein the magnitude of a second cross product of the second updated partner velocity vector and the transit velocity vector is less than the magnitude of the first cross product.

7. The eyewear of claim 1, wherein the one of the plurality of event trigger conditions includes detecting a change in transit direction from a first direction to a second direction, and wherein the corresponding one of the plurality of fitness partner actions includes setting an updated direction of the partner velocity vector in accordance with the change in transit direction.

8. The eyewear of claim 1, wherein the one of the plurality of event trigger conditions includes determining that a direction of vector projection of the virtual position vector onto a vector corresponding to the transit direction is opposite the transit direction.

9. The eyewear of claim 1, wherein the one of the plurality of event trigger conditions includes determining that a derivative of the transit pace exceeds a transit pace derivative threshold.

10. The eyewear of claim 1, wherein the fitness partner profile data includes a plurality of partner velocity vectors and a corresponding plurality of interval times, and wherein the virtual transit of the virtual fitness partner is displayed in accordance with the plurality of partner velocity vectors and a corresponding plurality of interval times.

11. The eyewear of claim 10, wherein the plurality of partner velocity vectors and the corresponding plurality of interval times are generated by the client application based on a plurality of previous transit velocity vectors and a corresponding plurality of previous timestamps generated by the motion data generator in a previous performance of the fitness activity.

12. The eyewear of claim 11, wherein the communication interface transmits a plurality of transit velocity vectors of the motion data and a corresponding plurality of timestamps corresponding to a duration of the fitness activity, wherein the client application accesses the plurality of transit velocity vectors of the motion data and the corresponding plurality of timestamps to generate aggregate fitness activity data, wherein the client application updates fitness activity history data in response to generating the aggregate fitness activity data, and wherein the fitness activity history data includes a plurality of aggregate fitness activity data corresponding to a plurality of performances of the fitness activity by the user.

13. The eyewear of claim 12, wherein the fitness partner profile data is generated based on selecting one of the plurality of performances of the fitness activity in the fitness activity history data.

14. The eyewear of claim 12, wherein the fitness activity history data includes route data corresponding to each of the plurality of performances of the fitness activity, wherein generating fitness partner profile data includes determining a current route of the fitness activity, and wherein generating the fitness partner profile data further includes identifying one of the plurality of performances of the fitness activity with corresponding route data that compares favorably to the current route.

15. The eyewear of claim 14, further comprising a geolocation sensor, wherein the communication interface further transmits a plurality of locations collected by the geolocation sensor corresponding to the plurality of transit velocity vectors, and wherein identifying one of the plurality of performances of the fitness activity with a corresponding location that compares favorably to the current route includes determining that a current location collected by the geolocation sensor compares favorably to one of the plurality of locations indicated in the fitness activity history data.

16. The eyewear of claim 12, wherein the client device communicates bidirectionally with a server via a wireless network, wherein the server stores a plurality of user profiles corresponding to a plurality of users, wherein the plurality of transit velocity vectors and the corresponding plurality of timestamps are transmitted from the client device to the server via a wireless network, wherein the server updates a first one of the plurality of user profiles corresponding to the user in response to receiving the plurality of transit velocity vectors and the corresponding plurality of timestamps, wherein the server transmits profile data stored in a second one of the plurality of user profiles to the client device, wherein the profile data includes a second plurality of transit velocity vectors and a second corresponding plurality of timestamps, and wherein the plurality of partner velocity vectors and the corresponding plurality of interval times are generated by the client application based on the second plurality of transit velocity vectors and the second corresponding plurality of timestamps.

17. The eyewear of claim 16, wherein the profile data includes second user appearance data, and wherein the virtual fitness partner is displayed to resemble a second user associated with the second one of the plurality of user profiles, based on the second user appearance data.

18. The eyewear of claim 1, wherein the display device is a heads-up display that projects the virtual fitness partner onto the at least one translucent lens.

19. A method for execution by a mobile communication device that includes a memory, at least one processor, and a short range wireless transceiver, wherein the method is executed in conjunction with mobile application instructions stored by the memory that, when executed by the at least one processor, cause the mobile communication device to:
generate motion data based on sensor input to at least one motion sensor of the mobile communication device corresponding to motion of a user of the mobile communication device during performance of a fitness activity;
determine a transit velocity vector corresponding to a transit of the user during the fitness activity based on the motion data wherein the transit velocity vector that indicates a transit pace and a transit direction;
receive, via the short range wireless transceiver, head tracking data corresponding to head movement of the user, wherein the head tracking data is collected by at least one motion sensor integrated within eyewear worn by the user during the performance of the fitness activity, and wherein the eyewear transmits the head tracking data to the mobile communication device during the performance of the fitness activity;
determine a head orientation direction relative to the transit direction based on the head tracking data and the transit velocity vector;
generate relative velocity data based on the transit velocity vector and a partner velocity vector, wherein the partner velocity vector is determined based on fitness partner profile data stored in the memory;
determine a virtual position vector based on the relative velocity data that indicates a magnitude and a direction of a virtual position of a virtual fitness partner relative to a position of the user;
generate perspective data that indicates a display size and display coordinates, calculated based on the virtual position vector and the head orientation direction;
generate event trigger monitoring data based on the motion data, wherein the event trigger monitoring data indicates one of a plurality of fitness partner actions in response to determining that a corresponding one of a plurality of event trigger conditions has been met;
generate display data based on the perspective data, the event trigger monitoring data, and appearance data, wherein the appearance data is determined based on the fitness partner profile data; and
transmit the display data to the eyewear via the short range wireless transceiver, wherein the display data is displayed on at least one display device of eyewear to virtually superimpose the virtual fitness partner upon physical surroundings viewed by the user through at least one translucent lens of the eyewear to simulate performance of the fitness activity by the virtual fitness partner along a virtual transit within a physical vicinity of the user throughout the transit of the user, wherein the virtual fitness partner is depicted to perform the one of the plurality of fitness partner actions in accordance with the event trigger monitoring data.

20. A mobile communication device, comprising:

at least one processor;

a memory that stores client application instructions for execution by the at least one processor;

a touchscreen display device configured to display an interactive interface in conjunction with execution of the client application instructions, and further configured to receive user input to the interactive interface; and a short range wireless transceiver configured to communicate bidirectionally, via a short range wireless communication protocol, with a processing system integrated within eyewear worn by a user while performing a fitness activity;

wherein the client application instruction, when executed by the at least one processor, cause the mobile communication device to:

receive, via the short range wireless transceiver, sensor data from at least one motion sensor integrated within the eyewear;

determine a transit velocity vector based on the sensor data, corresponding to a transit of the user during performance of the fitness activity, wherein the transit velocity vector indicates a transit pace and a transit direction;

determine head tracking data based on the sensor data, corresponding to head movement of the user during performance of the fitness activity, wherein the head tracking data indicates a head orientation direction relative to the transit direction;

generate fitness partner profile data based on the user input to the interactive interface displayed by the touchscreen display device;

generate appearance data corresponding to an appearance of a virtual fitness partner, wherein the appearance data is determined based on the fitness partner profile data;

generate perspective data that indicates a display size and display coordinates calculated based on a virtual position vector and the head orientation direction, wherein the virtual position vector is determined based on calculating relative velocity data based on the transit velocity vector and a partner velocity vector, and wherein the virtual position vector indicates a magnitude and a direction of a virtual position of the virtual fitness partner relative to a position of the user;

generate event trigger monitoring data based on the sensor data, wherein the event trigger monitoring data indicates one of a plurality of fitness partner actions in response to determining that a corresponding one of a plurality of event trigger conditions has been met;

generate display data based on the perspective data, the event trigger monitoring data, and the appearance data; and transmit the display data to the eyewear via the short range wireless transceiver, wherein the display data is displayed on at least one display device of eyewear to virtually superimpose the virtual fitness partner upon physical surroundings viewed by the user through at least one translucent lens of the eyewear to simulate performance of the fitness activity by the virtual fitness partner along a virtual transit within a physical vicinity of the user throughout the transit of the user, wherein the virtual fitness partner is depicted to perform the one of the plurality of fitness partner actions in accordance with the event trigger monitoring data.

* * * * *